(12) United States Patent
Urbanski et al.

(10) Patent No.: US 8,680,122 B2
(45) Date of Patent: Mar. 25, 2014

(54) SUBSTITUTED PYRROLONES AS ALLOSTERIC MODULATORS OF GLUCOKINASE

(75) Inventors: Maud Urbanski, Flemington, NJ (US); Amy Xiang, Bridgewater, NJ (US); Roxanne Zeck, Whitehouse Station, NJ (US)

(73) Assignee: Janssen Pharmacetica N.V., Beerse (BE)

( * ) Notice: Subject to any disclaimer, the term of this patent is extended or adjusted under 35 U.S.C. 154(b) by 1744 days.

(21) Appl. No.: 11/554,532

(22) Filed: Oct. 30, 2006

(65) Prior Publication Data
US 2007/0099937 A1 May 3, 2007

Related U.S. Application Data

(60) Provisional application No. 60/732,369, filed on Nov. 1, 2005.

(51) Int. Cl.
*A61K 31/4439* (2006.01)
*C07D 401/12* (2006.01)

(52) U.S. Cl.
USPC .................................. 514/343; 546/278.7

(58) Field of Classification Search
USPC .................................. 546/278.7; 514/343
See application file for complete search history.

(56) References Cited

FOREIGN PATENT DOCUMENTS

| WO | WO 01/16122 A1 | 3/2001 |
|----|----|----|
| WO | WO 01/16123 A1 | 3/2001 |
| WO | WO 02/48106 A2 | 6/2002 |
| WO | WO 03/055482 A1 | 7/2003 |

OTHER PUBLICATIONS

Balant et al., "Metabolic Considerations, etc.," in Manfred ed., Burger's Mediciinal Chemistry and Drug Discovery, 5th ed. vol. 1: Principles and Practice, John Wiley & Sons, Inc., 1995, pp. 975-977.*
Fujisawa, G. et. al; "Therapeutic efficacy of non-peptide ADH antagonist OPC-31260 in SIADH rats." *Kidney Intl*; vol. 44; 1993; pp. 19-23.
Connolly, H. M. et al; "Valvular Heart Disease Associated with Fenfluramine-Phentermine." *New Eng. J. of Medicine*; vol. 337, 1997, No. 9, pp. 581-588.
Lowney, V. K. Obesity *Decision Resources Inc*. Mosaic Study #20, 2000.
Database Chemcats (online), Chemical Abstract Service, Columbus, Ohio, US. XP002425266 and, "Interchim Intermediates" 2005, Interchim, France.
PCT International Search Report No. PCT/US2006/042588 dated Mar. 23, 2007, which relates to U.S. Appl. No. 11/554,532.
Berge et al., "Pharmaceutical Salts.", J. Pharm. Sci., 1977, vol. 66(1), pp. 1-19.
Gould P.L., "Salt Selection for Basic Drugs.", International J. Pharm., 1986, vol. 33, pp. 201-217.
Nikitin and Andryukhova,"5-Chloro Substituted 1,5-Dihydro-2H-pyrrol-2-ones as Intermediates for the Efficient Synthesis of 5-Alkylamino, 5-Azido, 5-Alkoxyamino, and 5-Alkoxy Deriva tives.", Synthesis, 2001, No. 1, pp. 89-92.

* cited by examiner

*Primary Examiner* — Patricia L Morris
(74) *Attorney, Agent, or Firm* — Jeremy K. McKown

(57) ABSTRACT

The present invention relates to compounds of Formula (I),

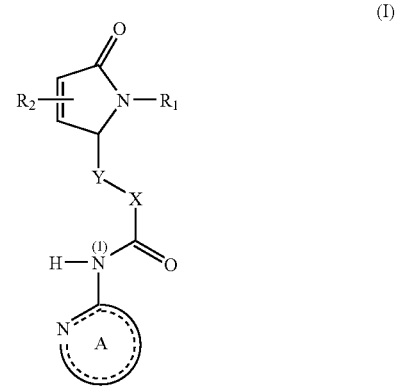

methods for preparing these compounds, compositions, intermediates and derivatives thereof and for treating glucokinase mediated disorders. More particularly, the compounds of the present invention are glucokinase modulators useful for treating disorders including, but not limited to, type II diabetes.

14 Claims, No Drawings

SUBSTITUTED PYRROLONES AS ALLOSTERIC MODULATORS OF GLUCOKINASE

CROSS REFERENCE TO RELATED APPLICATION

This application claims the benefit of U.S. provisional application Ser. No. 60/732,369 filed Nov. 1, 2005, which is incorporated by reference herein.

FIELD OF THE INVENTION

The present invention relates to certain novel compounds, methods for preparing compounds, compositions, intermediates and derivatives thereof and for treating metabolic disorders. More particularly, the compounds of the present invention are glucokinase modulators useful for treating, ameliorating or inhibiting the onset of metabolic disorders such as diabetes and obesity.

BACKGROUND OF THE INVENTION

Diabetes is a chronic disorder affecting carbohydrate, fat and protein metabolism in animals.

Type I diabetes mellitus, which comprises approximately 10% of all diabetes cases, was previously referred to as insulin-dependent diabetes mellitus ("IDDM") or juvenile-onset diabetes. This disease is characterized by a progressive loss of insulin secretory function by beta cells of the pancreas. This characteristic is also shared by non-idiopathic, or "secondary," diabetes having its origins in pancreatic disease. Type I diabetes mellitus is associated with the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Type II diabetes mellitus (non-insulin-dependent diabetes mellitus or "NIDDM") is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from the late-stage type II diabetes mellitus have a relative insulin insensitivity—that is patients have higher than predicted insulin levels for a given plasma glucose concentration. Type II diabetes mellitus is characterized by the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Obesity is rapidly becoming a major health crisis in developed countries as well as some regions of developing countries. The available evidence indicates that the prevalence of obesity in adults and children is growing at an alarming pace. In the developed world, estimates for 1999 suggest that the number of obese adults was approximately 88 million and growing at an annual rate of 2.8% (Decision Resources Report (2000), *Mosaic/Obesity* 20: 1-126). Obesity is believed to cause or exacerbate many health complications and social problems such as coronary heart disease, stroke, obstructive sleep apnea, gout, hyperlipidemia, osteoarthritis, reduced fertility, and impaired psychosocial function.

The widely held view that obesity is the result of a lack of self-control is slowly changing. Physicians are beginning to perceive obesity as a serious condition caused by a variety of complex messages involving signals for hunger, satiety, and determinants of energy consumption. It is now recognized that factors such as specific environmental cues, cultural norms, and genetic predisposition all contribute to excessive weight gain. The two major objectives for obesity treatment include a modest weight loss followed by appropriate weight maintenance, with the ultimate goal of reducing morbidity and mortality. A 5-10% reduction in body weight has been shown to produce clinically significant improvements in blood pressure, cholesterol, and blood glucose levels. General practitioners commonly cite three concerns with the existing treatments for obesity. These concerns include 1) the limited efficacy of current therapies, 2) poor side-effect profiles, and 3) non-compliance due to high cost of medication. Although obesity researchers have made great strides in understanding the fundamental causes of obesity, much remains to be done in the search for therapies with 1) increased efficacy, 2) better safety profiles, 3) lower cost, and 4) improved patient compliance.

Several products have been approved for treatment of obesity in the United States, such as the anorectic agent dexfenfluramine (d-FF or REDUX™) and fenfluramine, both 5-HT reuptake inhibitors, and the antiobesity agent sibutramine (MERIDIA™), a serotonin and noradrenaline uptake inhibitor. However, dexfenfluramine and fenfluramine were withdrawn from marketing on the basis of the reports that these drugs, when used in combination with phentermine, an anti-obesity agent that increases extraneuronal norepinephrine by enhancing its release, result in conditions including pulmonary hypertension and valvular heart disease (Connolly, H. M, Crary, J. M., McGoon, M. D. et al. Valvular heart disease associated with fenfluramine-phentermine. N. Engl. J. Med. (1997) 337:581-588). On the other hand, sibutramine, which reduces appetite, is only used by a small fraction of eligible obese patients due to the belief that anti-obesity drugs are unsafe. Thus, approved drugs for the treatment of a disorder that affects many millions are only moderately successful because of their widely recognized shortcomings.

Glucokinase ("GK" or "GLK") is a rate-limiting enzyme that catalyzes the conversion of glucose to glucose-6-phosphate, the first step in glucose metabolism. It is expressed in the pancreatic β-cells and hepatocytes, both of which are known to play critical roles in whole-body blood glucose homeostasis. The compounds of this invention act as glucokinase modulators. A modulator that raises the enzyme's affinity for glucose ($K_m$) and its velocity ($V_{max}$) would increase the flux of glucose metabolism in both cell types. Since pancreatic glucokinase modulation is coupled with an increase in insulin secretion, a modulator would be useful for the treatment of diabetes such as type II diabetes.

There is a continuing need for new glucokinase modulators. There is also a need for glucokinase modulators useful for the treatment of conditions including but not limited to metabolic disorders such as diabetes and obesity.

SUMMARY OF THE INVENTION

In its many embodiments, the present invention provides a novel class of compounds useful as, for example, glucokinase modulators, methods of preparing such compounds, pharmaceutical compositions comprising one or more such compounds, methods of preparing pharmaceutical compositions comprising one or more such compounds, and methods of treatment, prevention, inhibition or amelioration of one or more diseases associated with glucokinase using such compounds or pharmaceutical compositions.

One aspect of the present invention features a compound of Formula (I)

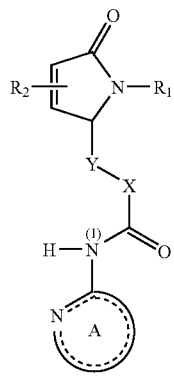

(I)

wherein
X is optionally substituted $C_{1-4}$alkylene;
Y is O, S, S(O), or N(H);
$R_1$ is H or $C_{1-6}$alkyl optionally substituted with optionally substituted aryl, optionally substituted heteroaryl, or optionally substituted heterocyclyl;
$R_2$ is 0-3 members independently selected from halo, —$OR_4$, —$SR_4$, —$S(O)_2$—$R_4$, carboxy, nitro, hydroxyl, amido, optionally substituted $C_{1-6}$alkyl, optionally substituted $C_{2-6}$alkenyl, optionally substituted $C_{2-6}$alkynyl, and amino optionally substituted with optionally substituted $C_{1-6}$alkyl, optionally substituted aryl, optionally substituted $C_{5-6}$heteroaryl, or optionally substituted $C_{5-8}$heterocyclyl, wherein $R_4$ is selected from H, $C_{1-6}$alkyl, aryl, heteroaryl, and heterocyclyl; and
A is heteroaryl or heterocyclyl, said heteroaryl being connected to N(1) through a ring carbon atom adjacent to a ring nitrogen, said heterocyclyl being connected to N(1) through a carbon atom that is double-bonded to a ring nitrogen, and additionally said heteroaryl and heterocyclyl having an additional 0 to 3 heteroatoms selected from O, S, and N, wherein one or more ring nitrogen atoms in said heteroaryl or heterocyclyl can be optionally in an N-oxide form, and said heteroaryl or heterocyclyl being further optionally substituted with 1 or 2 members selected from optionally substituted $C_{1-4}$alkyl, optionally substituted $C_{2-4}$alkenyl, halo, —CN, aryl, heteroaryl, heterocyclyl, —$SO_3H$, —C(O)OH, —C(O)O—$C_{1-4}$alkyl, —$OR_4$, —$SR_4$, —C(O)$R_4$, —N($R_4$)($R_5$), —C(O)—N($R_4$)($R_5$), —$S(O)_2$—$R_4$, and —$S(O)_2$—N($R_4$)($R_5$), wherein $R_4$ and $R_5$ are independently selected from H, $C_{1-6}$alkyl, aryl, heteroaryl, and heterocyclyl;
or an optical isomer, enantiomer, diastereomer, racemate, prodrug or pharmaceutically acceptable salt thereof.

Another aspect of the present invention features a pharmaceutical composition comprising at least one compound of Formula (I) and at least one pharmaceutically acceptable carrier.

One embodiment of the invention is a method for treating or ameliorating a glucokinase-mediated condition in a subject in need thereof comprising administering to the subject a therapeutically effective amount of at least one compound of Formula (I). Particularly, it is an embodiment of the invention to provide a method for treating, preventing or ameliorating a condition selected from diabetes, obesity, and associated symptoms or complications thereof in a subject in need thereof, comprising administering to said subject a therapeutically effective amount of (a) at least one compound of Formula (I); and (b) at least one additional agent selected from an anti-diabetic agent, a lipid lowering agent, an anti-thrombotic agent, and a blood pressure lowering agent, said co-administration being in any order. In one embodiment the additional agent is a glucokinase modulator.

Another embodiment of the invention is a method for preventing or inhibiting the onset of a glucokinase-mediated condition in a subject in need thereof, comprising administering to said subject a therapeutically effective amount of (a) at least one compound of Formula (I); and (b) at least one additional agent selected from an anti-diabetic agent, a lipid lowering agent, an anti-thrombotic agent, and a blood pressure lowering agent, said co-administration being in any order and the combined amounts providing the desired prophylactic effect. In one embodiment the additional agent is also a glucokinase modulator.

It is a further embodiment of the invention to provide a process for making a pharmaceutical composition comprising admixing any of the compounds according to Formula (I) and a pharmaceutically acceptable carrier.

Another embodiment of the invention is a method for treating or ameliorating glucokinase-mediated diseases such as diabetes ((including, but not limited to IDDM, NIDDM, IGT (Impaired Glucose Tolerance), IFG (Impaired Fasting Glucose)), obesity, and Syndrome X (or Metabolic Syndrome). A further embodiment of the invention is a method for treating or ameliorating the associated symptoms or complications of diabetes, obesity and/or Syndrome X, including, but not limited to hyperglycemia, elevated blood glucose level, and insulin resistance.

Additional embodiments and advantages of the invention will become apparent from the detailed discussion, examples, and claims below.

DETAILED DESCRIPTION OF THE INVENTION

This invention relates to novel glucokinase modulators and compositions thereof for treatment or prophylaxis of conditions such as diabetes, obesity, and associated symptoms or complications thereof.

One aspect of the present invention features a compound of Formula (I)

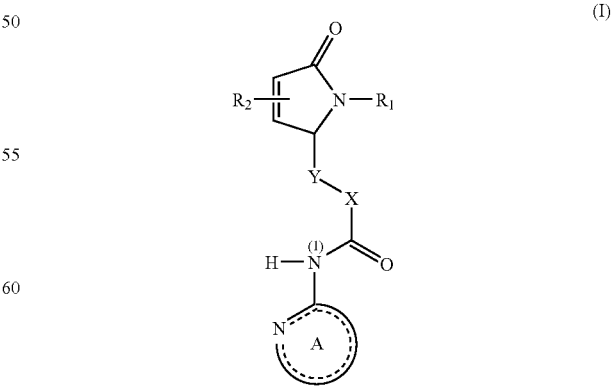

(I)

wherein
X is optionally substituted $C_{1-4}$alkylene;
Y is O, S, S(O), or N(H);

R₁ is H or $C_{1-6}$alkyl optionally substituted with optionally substituted aryl, optionally substituted heteroaryl, or optionally substituted heterocyclyl;

R₂ is 0-3 members independently selected from halo, —OR₄, —SR₄, —S(O)₂—R₄, carboxy, nitro, hydroxyl, amido, optionally substituted $C_{1-6}$alkyl, optionally substituted $C_{2-6}$alkenyl, optionally substituted $C_{2-6}$alkynyl, and amino optionally substituted with optionally substituted $C_{1-6}$alkyl, optionally substituted aryl, optionally substituted $C_{5-6}$heteroaryl, or optionally substituted $C_{5-8}$heterocyclyl, wherein R₄ is selected from H, $C_{1-6}$alkyl, aryl, heteroaryl, and heterocyclyl; and A is heteroaryl or heterocyclyl, said heteroaryl being connected to N(1) through a ring carbon atom adjacent to a ring nitrogen, said heterocyclyl being connected to N(1) through a carbon atom that is double-bonded to a ring nitrogen, and additionally said heteroaryl and heterocyclyl having an additional 0 to 3 heteroatoms selected from O, S, and N, wherein one or more ring nitrogen atoms in said heteroaryl or heterocyclyl can be optionally in an N-oxide form, and said heteroaryl or heterocyclyl being further optionally substituted with 1 or 2 members selected from optionally substituted $C_{1-4}$alkyl, optionally substituted $C_{2-4}$alkenyl, halo, —CN, aryl, heteroaryl, heterocyclyl, —SO₃H, —C(O)OH, —C(O)O—$C_{1-4}$alkyl, —OR₄, —SR₄, —C(O)R₄, —N(R₄)(R₅), —C(O)—N(R₄)(R₅), —S(O)₂—R₄, and —S(O)₂—N(R₄)(R₅), wherein R₄ and R₅ are independently selected from H, $C_{1-6}$alkyl, aryl, heteroaryl, and heterocyclyl;

or an optical isomer, enantiomer, diastereomer, racemate, prodrug or pharmaceutically acceptable salt thereof.

In particular, the present invention features a compound of Formula (I) wherein

R₁ is $C_{1-6}$alkyl optionally substituted with optionally substituted $C_6$- or $C_{10}$-aryl or optionally substituted $C_{4-10}$heteroaryl;

A is heteroaryl or heterocyclyl, said heteroaryl being connected to N(1) through a ring carbon atom adjacent to a ring nitrogen, said heterocyclyl being connected to N(1) through a carbon atom that is double-bonded to a ring nitrogen, and additionally said heteroaryl and heterocyclyl having an additional 0 to 2 heteroatoms selected from S and N, wherein one or more ring nitrogen atoms in said heteroaryl or heterocyclyl can be optionally in an N-oxide form, and said heteroaryl or heterocyclyl being further optionally substituted with 1 or 2 members selected from optionally substituted $C_{1-4}$alkyl, optionally substituted $C_{2-4}$alkenyl, halo, —CN, optionally substituted $C_{6-10}$aryl, —C(O)OH, —C(O)O—$C_{1-4}$alkyl, —OR₄, —C(O)R₄, —S(O)₂—R₄, and —S(O)₂—N(R₄)(R₅), wherein R₄ and R₅ are independently selected from H, $C_{1-6}$alkyl, aryl, heteroaryl, and heterocyclyl;

X is optionally substituted $C_{1-2}$ alkylene; and

Y is O or S;

or an optical isomer, enantiomer, diastereomer, racemate, prodrug or pharmaceutically acceptable salt thereof.

Particularly, the present invention features a compound of Formula (I) wherein R₁ is $C_{1-6}$alkyl substituted with optionally substituted aryl. More particularly, R₁ is methyl substituted with phenyl or $C_{4-8}$heteroaryl, said phenyl or $C_{4-8}$heteroaryl being optionally substituted with OH, $C_{1-3}$alkyl, —N(R₄)(R₅), halo, alkoxy, —C(O)O—$C_{1-4}$alkyl, or —NO₂.

Particularly, the present invention features a compound of Formula (I) wherein A is heteroaryl having 1-2 nitrogen atoms. Particularly, the present invention features a compound of Formula (I) wherein B is an optionally substituted heteroaryl selected from

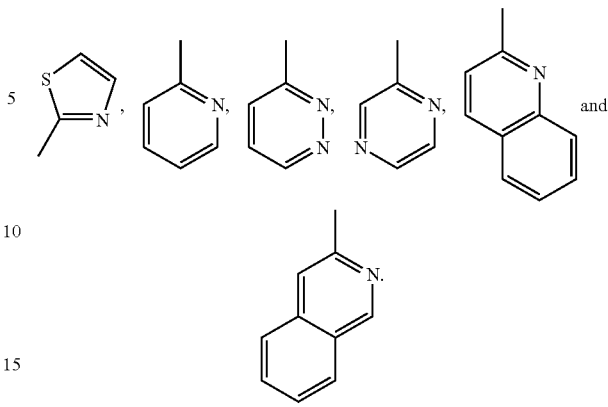

More particularly, one or more ring nitrogen atoms may optionally be in an N-oxide form. Specifically, an embodiment of the present invention is

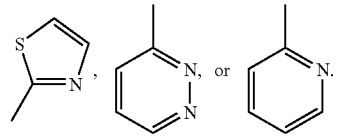

Particularly, A is substituted with 0-2 members selected from halo, $C_{1-4}$alkyl, substituted $C_{1-4}$alkyl, —CN, aryl, substituted aryl, —C(O)OH, —C(O)R₄, —C(O)O—$C_{1-4}$alkyl, —C(O)—N(R₄)(R₅), and —S(O)₂—N(R₄)(R₅), wherein R₄ and R₅ are as described above. In particular, A is substituted with 0-2 members selected from F, Cl, Br, —CH₃, —CH₂—CH₃, —CF₃, —CH₂—C(O)OH, —CN, —C(O)—CH₃, —CH₂—O—CH₂—O—CH₃, unsubstituted phenyl, halo substituted aryl, —C(O)OH, —C(O)O—CH₃, —CH₂—C(O)O—CH₂—CH₃, —C(O)O—CH₂—CH₃, —C(O)—NH₂, and —S(O)₂—NH₂.

Particularly, the present invention features a compound of Formula (I) wherein X is optionally substituted $C_{1-2}$ alkylene. In particular, X is —C(H)(CH₃)— or —CH₂—.

Particularly, the present invention features a compound of Formula (I) wherein Y is S.

Particularly, the present invention features a compound of Formula (I) wherein Y is N(H) or S(O).

Particularly, the present invention features a compound of Formula (I) wherein Y is O.

Particularly, A is N-containing heteroaryl wherein a ring nitrogen in ring A may optionally be in an N-oxide form.

More particularly, the present invention features a compound of Formula (I) wherein R₁ is —CH₂—OR—CH(CH₃)— substituted with

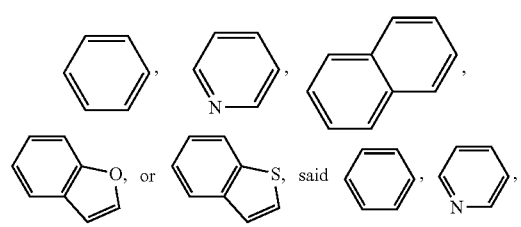

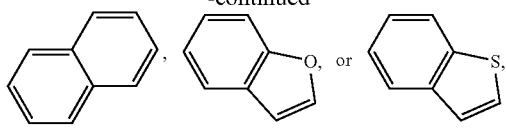

being optionally substituted with F, OH, —CH₃, —O—CH₃, —NO₂, —O—CH(CH₃)₂, and —C(O)—NH₂;

A is an optionally substituted member selected from

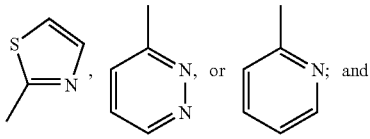

X is methylene.

In particular, A is substituted with 0-2 members selected from halo, $C_{1-4}$alkyl, substituted $C_{1-4}$alkyl, aryl, substituted aryl, —C(O)OH, —C(O)R₄, —C(O)—N(R₄)(R₅), —C(O) O—$C_{1-4}$alkyl, and —S(O)₂—N(R₄)(R₅), wherein R₄ and R₅ are as described above. More particularly, A is substituted with 0-2 members selected from —CH₃, —C(O)OH, —C(O) O—CH₃, and —C(O)—NH₂.

In one aspect, the present invention features a compound of Formula (I) selected from:

6-{2-[1-(4-Methoxy-benzyl)-3,4-dimethyl-5-oxo-2,5-dihydro-1H-pyrrol-2-ylsulfanyl]-acetylamino}-nicotinic acid methyl ester;

2-[1-(2,3-Dihydro-benzofuran-5-ylmethyl)-3,4-dimethyl-5-oxo-2,5-dihydro-1H-pyrrol-2-ylsulfanyl]-N-pyridin-2-yl-acetamide;

6-{2-[1-(4-Methoxy-benzyl)-3,4-dimethyl-5-oxo-2,5-dihydro-1H-pyrrol-2-ylsulfanyl]-acetylamino}-nicotinic acid;

6-{2-[1-(4-Fluoro-benzyl)-3,4-dimethyl-5-oxo-2,5-dihydro-1H-pyrrol-2-ylsulfanyl]-acetylamino}-nicotinic acid methyl ester; and 6-{2-[1-(2,3-Dihydro-benzofuran-5-yl methyl)-3,4-dimethyl-5-oxo-2,5-dihydro-1H-pyrrol-2-ylsulfanyl]-acetylamino}-nicotinic acid methyl ester.

Another aspect of the present invention features a pharmaceutical composition comprising at least one compound of Formula (I) and at least one pharmaceutically acceptable carrier. In another aspect of the invention, the pharmaceutical composition further comprises at least one additional agent, drug, medicament, antibody and/or inhibitor for treating, ameliorating and/or preventing a glucokinase-mediated condition. In one embodiment of the pharmaceutical composition of the present invention, at least one compound of Formula (I) is selected from:

6-{2-[1-(4-Methoxy-benzyl)-3,4-dimethyl-5-oxo-2,5-dihydro-1H-pyrrol-2-ylsulfanyl]-acetylamino}-nicotinic acid methyl ester;

2-[1-(2,3-Dihydro-benzofuran-5-ylmethyl)-3,4-dimethyl-5-oxo-2,5-dihydro-1H-pyrrol-2-ylsulfanyl]-N-pyridin-2-yl-acetamide;

6-{2-[1-(4-Methoxy-benzyl)-3,4-dimethyl-5-oxo-2,5-dihydro-1H-pyrrol-2-ylsulfanyl]-acetylamino}-nicotinic acid;

6-{2-[1-(4-Fluoro-benzyl)-3,4-dimethyl-5-oxo-2,5-dihydro-1H-pyrrol-2-ylsulfanyl]-acetylamino}-nicotinic acid methyl ester; and 6-{2-[1-(2,3-Dihydro-benzofuran-5-yl methyl)-3,4-dimethyl-5-oxo-2,5-dihydro-1H-pyrrol-2-ylsulfanyl]-acetylamino}-nicotinic acid methyl ester.

In another embodiment of the invention a method is disclosed for treating, preventing or ameliorating a glucokinase-mediated condition in a subject in need thereof comprising administering to the subject a therapeutically effective amount of at least one compound of Formula (I). An embodiment of the invention includes a method for treating, preventing or ameliorating a glucokinase modulator-mediated condition selected from diabetes, obesity, and associated symptoms or complications thereof in a subject in need thereof, comprising administering to said subject a therapeutically effective amount of at least one compound of Formula (I).

A further embodiment of the invention is a method for treating, preventing or ameliorating a glucokinase modulator-mediated condition selected from IDDM, NIDDM, IGT (Impaired Glucose Tolerance), IFG (Impaired Fasting Glucose), Syndrome X (or Metabolic Syndrome), obesity, hyperglycemia, elevated blood glucose level, and insulin resistance in a subject in need thereof, comprising administering to said subject a therapeutically effective amount of at least one compound of Formula (I).

One embodiment of the invention is a method of treating diabetes, obesity, and associated symptoms or complications thereof.

Furthermore, glucokinase modulators can be co-administered with a second agent other than a glucokinase modulator; such second agent can be, for example, an anti-diabetic agent, a lipid lowering agent, a blood pressure lowering agent, direct thrombin inhibitor (DTI), and an anti-thrombotic agent (e.g., aspirin, heparins, glycoprotein IIb-IIIa inhibitors, or Factor Xa inhibitors).

Particularly, it is an embodiment of the invention to provide a method for treating, preventing or ameliorating a condition selected from diabetes, obesity, and associated symptoms or complications thereof in a subject in need thereof, comprising administering to said subject a therapeutically effective amount of (a) at least one compound of Formula (I); and (b) at least one additional agent selected from a second glucokinase modulator, an anti-diabetic agent, a lipid lowering agent, an anti-thrombotic agent, and a blood pressure lowering agent, said administration being in any order. In one embodiment, the additional agent is a second glucokinase modulator. In a further embodiment, the additional agent is an anti-diabetic agent. In another embodiment, the additional agent is a lipid lowering agent. In still another embodiment, the additional agent is an anti-thrombotic agent. In yet another embodiment, the additional agent is a blood pressure lowering agent.

Another embodiment of the invention is a method for inhibiting the onset of a glucokinase modulator mediated condition in a subject in need thereof, comprising administering to said subject a therapeutically effective amount of at least one compound of Formula (I). Another embodiment of the invention is a method for inhibiting the onset of a condition selected from diabetes, obesity, and associated symptoms or complications thereof in a subject in need thereof, comprising administering to said subject an effective amount of (a) at least one compound of Formula (I); and (b) at least one compound selected from the group consisting of a glucokinase modulator, an anti-diabetic agent, a lipid lowering agent, an anti-thrombotic agent, and a blood pressure lowering agent, said co-administration being in any order and the combined amounts providing the desired prophylactic effect.

A further embodiment of the invention is a method for inhibiting the onset of a condition selected from diabetes such as IDDM and NIDDM, hyperglycemia, IGT (Impaired Glucose Tolerance), IFG (Impaired Fasting Glucose), Syndrome X (or Metabolic Syndrome), elevated blood glucose, and insulin resistance in a subject in need thereof, comprising administering to said subject a prophylactically effective amount of at least one compound of Formula (I). In one embodiment, the additional agent is a second glucokinase modulator. In a further embodiment, the additional agent is an anti-diabetic agent. In another embodiment, the additional agent is a lipid lowering agent. In still another embodiment, the additional agent is an anti-thrombotic agent. In yet another embodiment, the additional agent is a blood pressure lowering agent.

It is a further embodiment of the invention to provide a process for making a pharmaceutical composition comprising admixing any of the compounds according to Formula (I) and a pharmaceutically acceptable carrier.

In a further embodiment of the invention, a method for treating, preventing or ameliorating a glucokinase-mediated condition in a subject in need thereof comprising administering to the subject a therapeutically effective amount of at least one compound of Formula (I), wherein the therapeutically effective amount of the compound of Formula (I) is from about 0.001 mg/kg/day to about 10 mg/kg/day.

In a further embodiment of the invention, a method for inhibiting the onset of a glucokinase-mediated condition in a subject in need thereof comprising administering to the subject a therapeutically effective amount of at least one compound of Formula (I), wherein the therapeutically effective amount of the compound of Formula (I) is from about 0.001 mg/kg/day to about 10 mg/kg/day.

The invention is further described below.

A) Terms

Some terms are defined below and by their usage throughout this disclosure.

Unless otherwise noted, "alkyl" as used herein, whether used alone or as part of a substituent group, refers to a saturated or unsaturated, branched, straight-chain or cyclic monovalent hydrocarbon radical derived by the removal of one hydrogen atom from a single carbon atom of a parent alkane. Typical alkyl groups include, but are not limited to, methyl; ethyls such as ethanyl; propyls such as propan-1-yl, propan-2-yl, cyclopropan-1-yl.; butyls such as butan-1-yl, butan-2-yl, 2-methyl-propan-1-yl, 2-methyl-propan-2-yl, cyclobutan-1-yl and the like. In preferred embodiments, the alkyl groups are $C_{1-6}$alkyl, with $C_{1-3}$ being particularly preferred. "Alkoxy" radicals are oxygen ethers formed from the previously described straight, branched, or cyclic chain alkyl groups. In some embodiments, the alkyl or alkoxy are independently substituted with one to five, preferably one to three groups including, but not limited to, oxo, amino, alkoxy, carboxy, nitro, hydroxyl, and halo (F, Cl, Br, or I).

The term "alkenyl" refers to an unsaturated branched, straight-chain or cyclic monovalent hydrocarbon radical, which has at least one carbon-carbon double bond, derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl is substituted with one to five, preferably one to three groups including, but not limited to, amino, alkoxy, carboxy, nitro, hydroxyl, and halo.

The term "alkynyl" refers to an unsaturated branched, straight-chain or cyclic monovalent hydrocarbon radical, which has at least one carbon-carbon triple bond, derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In some embodiments, the alkynyl is substituted with one to five, preferably one to three groups including, but not limited to, amino, alkoxy, carboxy, nitro, hydroxyl, and halo.

The term "alkylene" denotes straight, branched, or cyclic alkyl diradical, or straight or branched alkenyl diradical, or straight or branched alkynyldiradical, wherein the valencies are located on the two termini. "Alkylene" is optionally substituted with one to five, preferably one to three groups including, but not limited to, optionally substituted $C_{1-3}$alkyl and halo (F, Cl, Br, or I).

The term "cycloalkyl," as used herein, refers to a stable, saturated or partially saturated monocyclic or bicyclic ring system containing from 3 to 8 ring carbons and preferably 5 to 7 ring carbons. Examples of such cyclic alkyl rings include cyclopropyl, cyclobutyl, cyclopentyl, cyclohexyl or cycloheptyl. In some embodiments, the cycloalkyl is substituted with one to five, preferably one to three groups including, but not limited to, amino, carboxy, nitro, hydroxyl, and halo.

The term "oxo" whether used alone or as part of a substituent group refers to an O= to either a carbon or a sulfur atom. For example, phthalimide and saccharin are examples of compounds with oxo substituents.

The term "aryl," as used herein, refers to aromatic groups comprising a stable six-membered monocyclic, or ten-membered bicyclic or fourteen-membered tricyclic aromatic ring system which consists of carbon atoms. Examples of aryl groups include, but are not limited to, phenyl or naphthalenyl. In some embodiments, "aryl" is substituted. For instance, "aryl" can be substituted with, e.g., optionally substituted $C_{1-6}$alkyl, $C_{2-6}$alkenyl, $C_{2-6}$alkynyl, halo, nitro, hydroxyl, ethynyl, —CN, aryl, heteroaryl, heterocyclyl, —SO$_3$H, —C(O)OH, —C(O)O—$C_{1-4}$alkyl, —C(O)NR'R", —SR', —OR', —C(O)R', —N(R')(R"), —S(O)$_2$—R', and —S(O)$_2$—N(R')(R"), wherein R' and R" are independently selected from H, $C_{1-6}$-alkyl, aryl, heteroaryl, and/or heterocyclyl.

The term "heteroaryl" refers to a monovalent heteroaromatic radical derived by the removal of one hydrogen atom from a single atom of a parent heteroaromatic ring system. Typical heteroaryl groups include monocyclic and bicyclic systems where one or both rings is heteroaromatic Heteroaromatic rings may contain 1-4 heteroatoms selected from O, N, and S. Examples include but are not limited to, radicals derived from carbazole, imidazole, indazole, indole, indolizine, isoindole, isoquinoline, isothiazole, isoxazole, naphthyridine, oxadiazole, oxazole, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, "heteroaryl" is substituted. For instance, "heteroaryl" can be substituted with, e.g., optionally substituted $C_{1-6}$alkyl, $C_{2-6}$alkenyl, $C_{2-6}$alkynyl, halo, nitro, hydroxyl, ethynyl, —CN, aryl, heteroaryl, heterocyclyl, —SO$_3$H, —C(O)OH, —C(O)O—$C_{1-4}$alkyl, —C(O)NR'R"—OR', —SR'—C(O)R', —N(R')(R"), —S(O)$_2$—R', and —S(O)$_2$—N(R')(R"), wherein R' and R" are independently selected from H, $C_{1-6}$-alkyl, aryl, heteroaryl, and/or heterocyclyl.

The term "heterocyclyl" or "heterocycle" is a 3- to 8-member saturated, or partially saturated single or fused ring system which consists of carbon atoms and from 1 to 6 heteroatoms selected from N, O and S. The heterocyclyl group may be attached at any heteroatom or carbon atom which results in the creation of a stable structure. Example of heterocyclyl groups include, but are not limited to, 2-imidazoline, imidazolidine; morpholine, oxazoline, 2-pyrroline, 3-pyrroline, pyrrolidine, pyridone, pyrimidone, piperazine, piperidine, indoline, tetrahydrofuran, 2-pyrroline, 3-pyrroline, 2-imidazoline, 2-pyrazoline, indolinone, A "heterocyclyl" can be a partially unsaturated ring such as 2-pyrroline, 3-pyrroline, 2-imidazoline, 2-pyrazoline, indolinone, or. "Heterocyclyl" being connected to N(1), as shown in Formula (I), through a ring carbon atom that is double-bonded to a ring nitrogen can include, but is not limited to 4,5-dihydrothiazole, 3-psuedoindolone, and pyrimidone. In some embodiments, "heterocyclyl" or "heterocycle" are independently substituted. For instance, "heterocyclyl" or "heterocycle" can be substituted with, e.g., optionally substituted $C_{1-6}$alkyl, $C_{2-6}$alkenyl, $C_{2-6}$alkynyl, halo, nitro, hydroxyl, ethynyl, —CN, aryl, heteroaryl, heterocyclyl, —$SO_3H$, —C(O)OH, —C(O)O—$C_{1-4}$alkyl, C(O)NR'R", —OR', —SR', —C(O)R', —N(R')(R"), —S(O)$_2$—R', and —S(O)$_2$—N(R')(R"), wherein R' and R" are independently selected from H, $C_{1-6}$-alkyl, aryl, heteroaryl, and/or heterocyclyl.

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "allosteric modulator" as used herein, refers to a molecule that stabilizes conformations or forms of the glucokinase protein, through binding to a site remote from the catalytic site on the protein. This effect may be manifested through alteration of the catalytic nature of the protein. Experimentally, the effect can be observed by examining the degree of activation, or by deriving the $K_m$ or $V_{max}$, for the phosphorylation of glucose by glucokinase in the presence of the modulator. Alternatively, the effect of the allosteric modulator may be manifested through stabilization of glucokinase toward regulatory mechanisms in cellular systems or animals.

Diabetes, obesity, and associated symptoms or complications include such conditions as IDDM, NIDDM, IGT (Impaired Glucose Tolerance), IFG (Impaired Fasting Glucose), Syndrome X (or Metabolic Syndrome), hyperglycemia, elevated blood glucose level, and insulin resistance. IGT and IFG are also known as "prediabetic state."

Methods are known in the art for determining effective doses for therapeutic and prophylactic purposes for the disclosed pharmaceutical compositions or the disclosed drug combinations, whether or not formulated in the same composition. For therapeutic purposes, the term "therapeutically effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "therapeutically effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

The term "pharmaceutically acceptable salt" refers to non-toxic pharmaceutically acceptable salts (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The term "protecting groups" refer to those moieties known in the art that are used to mask functional groups; protecting groups may be removed during subsequent synthetic transformations or by metabolic or other in vivo administration conditions. During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known in the art.

B) Compounds

| STRUCTURE | COMPOUND # | NAME |
|---|---|---|
| 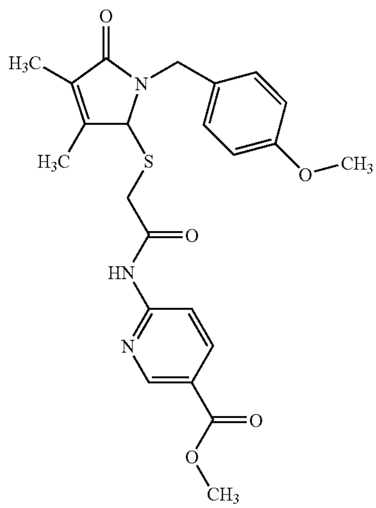 | 1 | 6-{2-[1-(4-Methoxy-benzyl)-3,4-dimethyl-5-oxo-2,5-dihydro-1H-pyrrol-2-ylsulfanyl]-acetylamino}-nicotinic acid methyl ester |
| 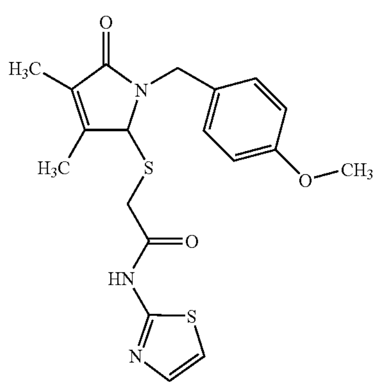 | 2 | 2-[1-(4-Methoxy-benzyl)-3,4-dimethyl-5-oxo-2,5-dihydro-1H-pyrrol-2-ylsulfanyl]-N-thiazol-2-yl-acetamide |
| 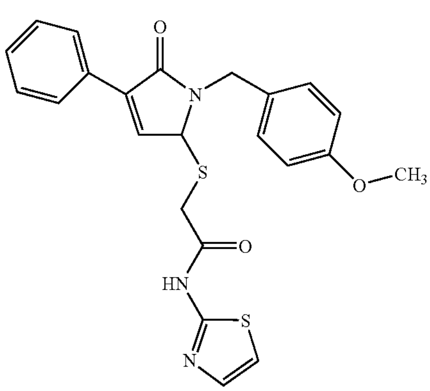 [SMILES: COc1ccc(CN2C(=O)C(c3ccccc3)=CC2SCC(=O)Nc2nccs2)cc1] | 3 | 2-[1-(4-Methoxy-benzyl)-5-oxo-4-phenyl-2,5-dihydro-1H-pyrrol-2-ylsulfanyl]-N-thiazol-2-yl-acetamide |

-continued

| STRUCTURE | COMPOUND # | NAME |
|---|---|---|
| 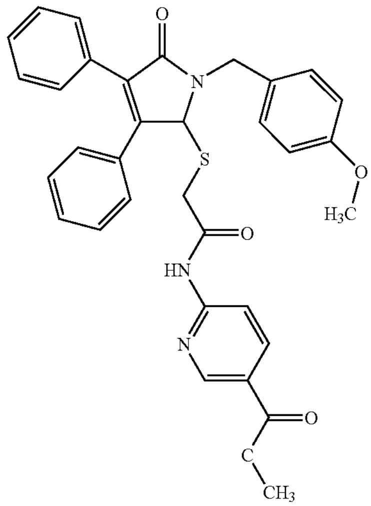 [SMILES: CCC(=O)c1ccc(NC(=O)CSC2C(c3ccccc3)=C(c3ccccc3)C(=O)N2Cc2ccc(OC)cc2)nc1] | 4 | 6-{2-[1-(4-Methoxy-benzyl)-5-oxo-3,4-diphenyl-2,5-dihydro-1H-pyrrol-2-ylsulfanyl]-acetylamino}-nicotinic acid methyl ester |
| 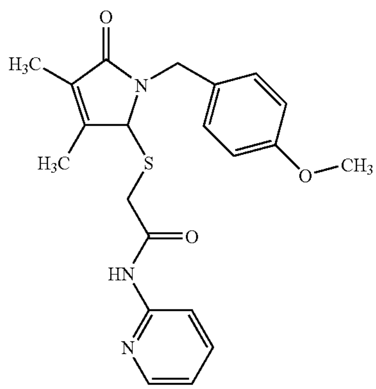 | 5 | 2-[1-(4-Methoxy-benzyl)-3,4-dimethyl-5-oxo-2,5-dihydro-1H-pyrrol-2-ylsulfanyl]-N-pyridin-2-yl-acetamide |
| 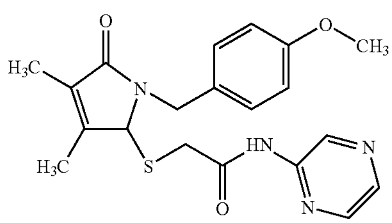 [SMILES: COc1ccc(CN2C(=O)C(C)=C(C)C2SCC(=O)Nc2cnccn2)cc1] | 6 | 2-[1-(4-Methoxy-benzyl)-3,4-dimethyl-5-oxo-2,5-dihydro-1H-pyrrol-2-ylsulfanyl]-N-pyrazin-2-yl-acetamide |
| 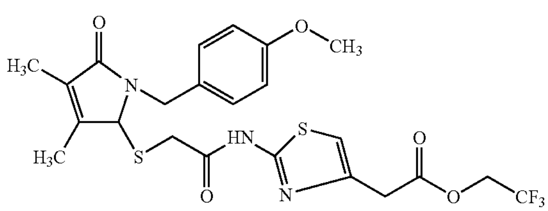 [SMILES: COc1ccc(CN2C(=O)C(C)=C(C)C2SCC(=O)Nc2nc(CC(=O)OCC(F)(F)F)cs2)cc1] | 7 | (2-{2-[1-(4-Methoxy-benzyl)-3,4-dimethyl-5-oxo-2,5-dihydro-1H-pyrrol-2-ylsulfanyl]-acetylamino}-thiazol-4-yl)-acetic acid ethyl ester |
| 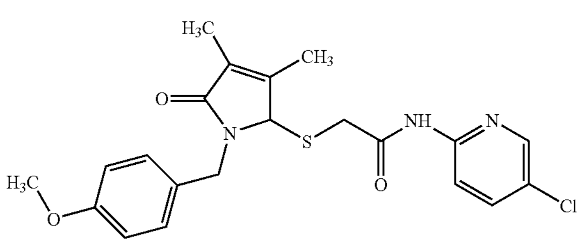 [SMILES: COc1ccc(CN2C(=O)C(C)=C(C)C2SCC(=O)Nc2ccc(Cl)cn2)cc1] | 8 | N-(5-Chloro-pyridin-2-yl)-2-[1-(4-methoxy-benzyl)-3,4-dimethyl-5-oxo-2,5-dihydro-1H-pyrrol-2-ylsulfanyl]-acetamide |

| STRUCTURE | COMPOUND # | NAME |
|---|---|---|
| 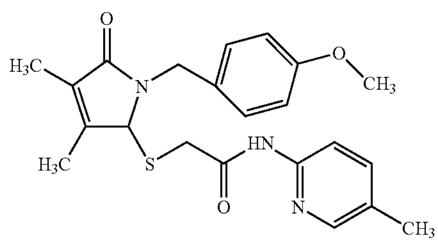 | 9 | 2-[1-(4-Methoxy-benzyl)-3,4-dimethyl-5-oxo-2,5-dihydro-1H-pyrrol-2-ylsulfanyl]-N-(5-methyl-pyridin-2-yl)-acetamide |
| 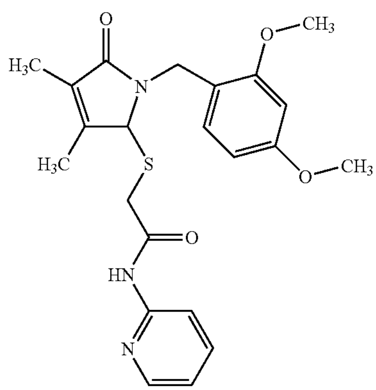 | 10 | 2-[1-(2,4-Dimethoxy-benzyl)-3,4-dimethyl-5-oxo-2,5-dihydro-1H-pyrrol-2-ylsulfanyl]-N-pyridin-2-yl-acetamide |
| 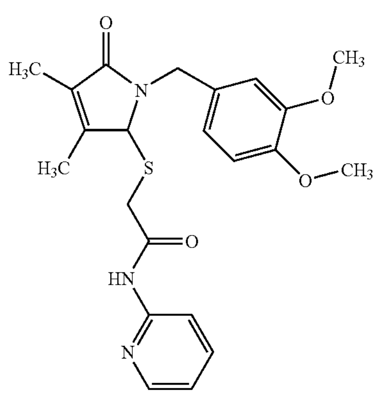 | 11 | 2-[1-(4-Fluoro-benzyl)-3,4-dimethyl-5-oxo-2,5-dihydro-1H-pyrrol-2-ylsulfanyl]-N-pyridin-2-yl-acetamide |
| 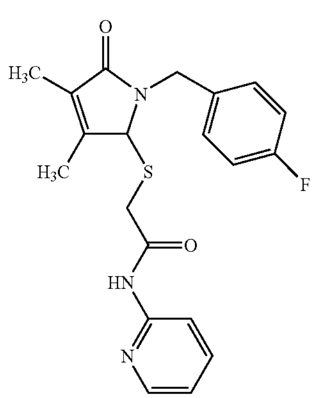 [SMILES: CC1=C(C)C(SCC(=O)Nc2ccccn2)N(Cc2ccc(F)cc2)C1=O] | 12 | 2-[1-(4-Fluoro-benzyl)-3,4-dimethyl-5-oxo-2,5-dihydro-1H-pyrrol-2-ylsulfanyl]-N-pyridin-2-yl-acetamide |

-continued

| STRUCTURE | COMPOUND # | NAME |
|---|---|---|
| 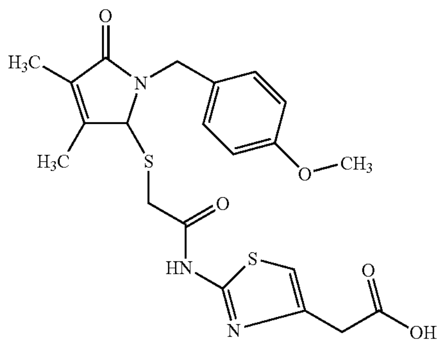 [SMILES: COc1ccc(CN2C(=O)C(C)=C(C)C2SCC(=O)Nc2nc(CC(=O)O)cs2)cc1] | 14 | (2-{2-[1-(4-Methoxy-benzyl)-3,4-dimethyl-5-oxo-2,5-dihydro-1H-pyrrol-2-ylsulfanyl]-acetylamino}-thiazol-4-yl)-acetic acid |
| 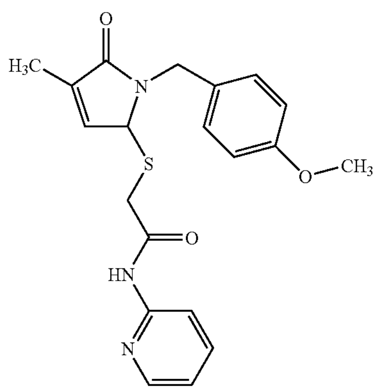 | 15 | 2-[1-(4-Methoxy-benzyl)-4-methyl-5-oxo-2,5-dihydro-1H-pyrrol-2-ylsulfanyl]-N-pyridin-2-yl-acetamide |
| 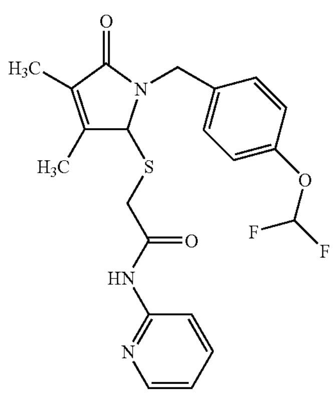 [SMILES: CC1=C(C)C(SCC(=O)Nc2ccccn2)N(Cc2ccc(OC(F)F)cc2)C1=O] | 16 | 2-[1-(4-Difluoromethoxy-benzyl)-3,4-dimethyl-5-oxo-2,5-dihydro-1H-pyrrol-2-ylsulfanyl]-N-pyridin-2-yl-acetamide |
| 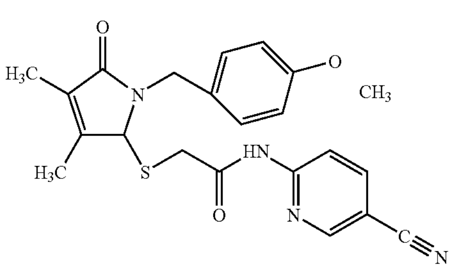 | 17 | N-(5-Cyano-pyridin-2-yl)-2-[1-(4-methoxy-benzyl)-3,4-dimethyl-5-oxo-2,5-dihydro-1H-pyrrol-2-ylsulfanyl]-acetamide |

-continued

| STRUCTURE | COMPOUND # | NAME |
|---|---|---|
| 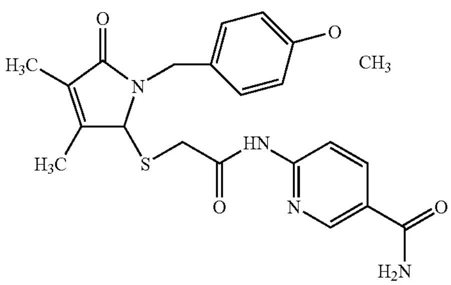 | 18 | 6-{2-[1-(4-Methoxy-benzyl)-3,4-dimethyl-5-oxo-2,5-dihydro-1H-pyrrol-2-ylsulfanyl]-acetylamino}-nicotinamide |
| 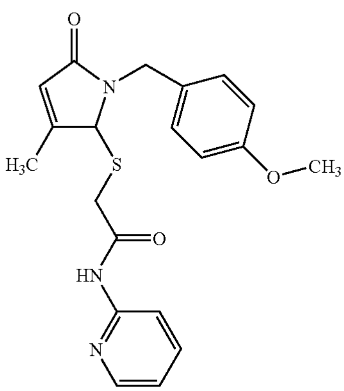 | 19 | 2-[1-(4-Methoxy-benzyl)-3-methyl-5-oxo-2,5-dihydro-1H-pyrrol-2-ylsulfanyl]-N-pyridin-2-yl-acetamide |
| 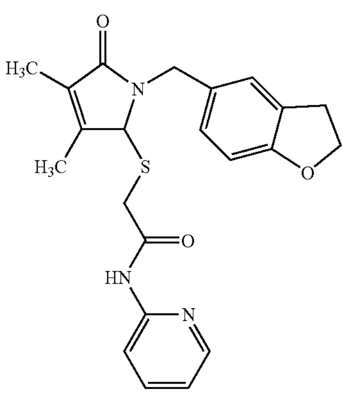 [SMILES: CC1=C(C)C(SCC(=O)Nc2ccccn2)N(Cc2ccc3c(c2)CCO3)C1=O] | 20 | 2-[1-(2,3-Dihydro-benzofuran-5-ylmethyl)-3,4-dimethyl-5-oxo-2,5-dihydro-1H-pyrrol-2-ylsulfanyl]-N-pyridin-2-yl-acetamide |
| 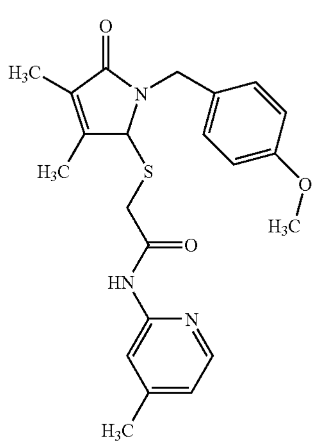 [SMILES: COc1ccc(CN2C(=O)C(C)=C(C)C2SCC(=O)Nc2cc(C)ccn2)cc1] | 21 | 2-[1-(4-Methoxy-benzyl)-3,4-dimethyl-5-oxo-2,5-dihydro-1H-pyrrol-2-ylsulfanyl]-N-(4-methyl-pyridin-2-yl)-acetamide |

-continued

| STRUCTURE | COMPOUND # | NAME |
|---|---|---|
| 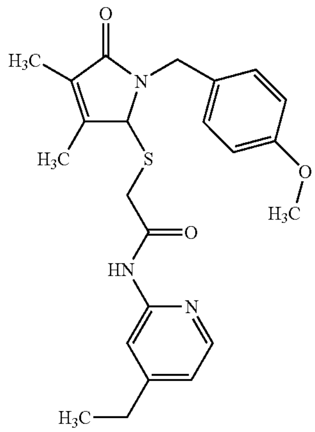 [SMILES: CCc1ccnc(NC(=O)CSC2C(C)=C(C)C(=O)N2Cc2ccc(OC)cc2)c1] | 22 | N-(4-Ethyl-pyridin-2-yl)-2-[1-(4-methoxy-benzyl)-3,4-dimethyl-5-oxo-2,5-dihydro-1H-pyrrol-2-ylsulfanyl]-acetamide |
| 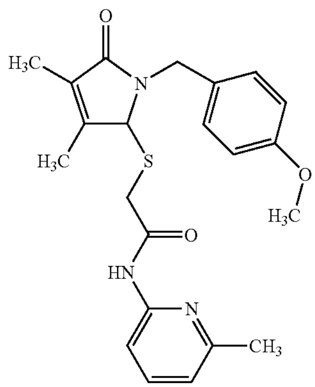 [SMILES: COc1ccc(CN2C(=O)C(C)=C(C)C2SCC(=O)Nc2cccc(C)n2)cc1] | 23 | 2-[1-(4-Methoxy-benzyl)-3,4-dimethyl-5-oxo-2,5-dihydro-1H-pyrrol-2-ylsulfanyl]-N-(6-methyl-pyridin-2-yl)-acetamide |
| 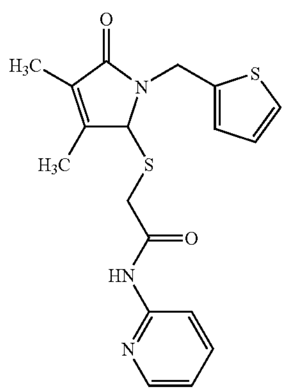 [SMILES: CC1=C(C)C(SCC(=O)Nc2ccccn2)N(Cc2cccs2)C1=O] | 24 | 2-(3,4-Dimethyl-5-oxo-1-thiophen-2-ylmethyl-2,5-dihydro-1H-pyrrol-2-ylsulfanyl)-N-pyridin-2-yl-acetamide |
| 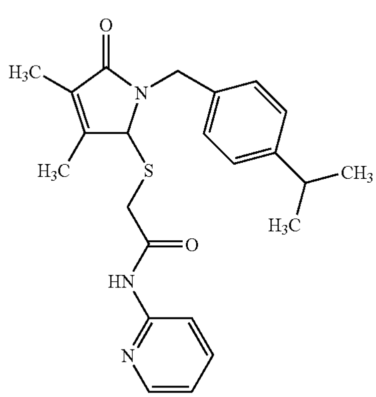 [SMILES: CC1=C(C)C(SCC(=O)Nc2ccccn2)N(Cc2ccc(C(C)C)cc2)C1=O] | 25 | 2-[1-(4-Isopropyl-benzyl)-3,4-dimethyl-5-oxo-2,5-dihydro-1H-pyrrol-2-ylsulfanyl]-N-pyridin-2-yl-acetamide |

-continued

| STRUCTURE | COMPOUND # | NAME |
|---|---|---|
| 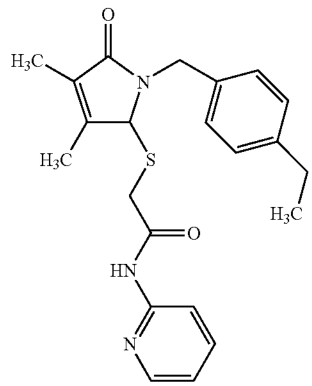 [SMILES: CCc1ccc(CN2C(=O)C(C)=C(C)C2SCC(=O)Nc2ccccn2)cc1] | 26 | 2-[1-(4-Ethyl-benzyl)-3,4-dimethyl-5-oxo-2,5-dihydro-1H-pyrrol-2-ylsulfanyl]-N-pyridin-2-yl-acetamide |
| 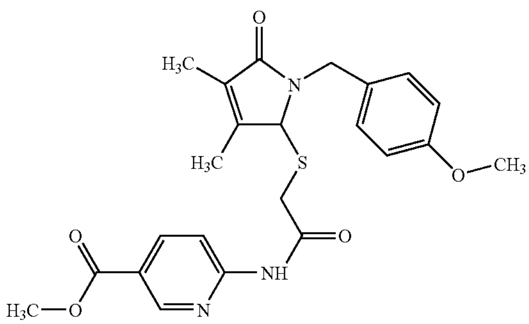 | 27 | 6-{2-[1-(4-Methoxy-benzyl)-3,4-dimethyl-5-oxo-2,5-dihydro-1H-pyrrol-2-yloxy]-acetylamino}-nicotinic acid methyl ester |
| 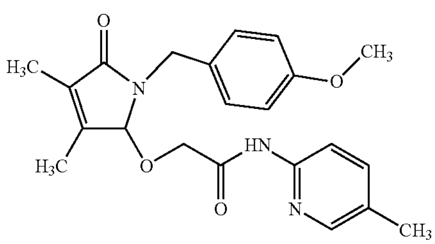 | 28 | 2-[1-(4-Methoxy-benzyl)-3,4-dimethyl-5-oxo-2,5-dihydro-1H-pyrrol-2-yloxy]-N-(5-methyl-pyridin-2-yl)-acetamide |
| 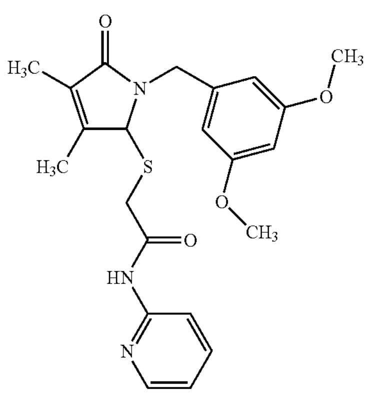 | 29 | 2-[1-(3,5-Dimethoxy-benzyl)-3,4-dimethyl-5-oxo-2,5-dihydro-1H-pyrrol-2-ylsulfanyl]-N-pyridin-2-yl-acetamide |
| 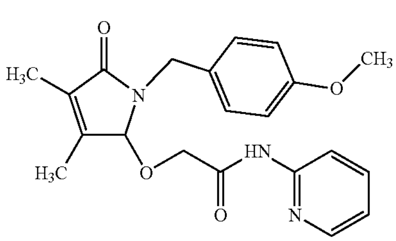 [SMILES: COc1ccc(CN2C(=O)C(C)=C(C)C2OCC(=O)Nc2ccccn2)cc1] | 30 | 2-[1-(4-Methoxy-benzyl)-3,4-dimethyl-5-oxo-2,5-dihydro-1H-pyrrol-2-yloxy]-N-pyridin-2-yl-acetamide |

-continued

| STRUCTURE | COMPOUND # | NAME |
|---|---|---|
| 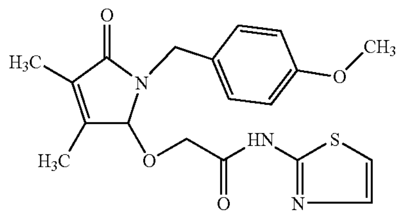 [SMILES: COc1ccc(CN2C(=O)C(C)=C(C)C2OCC(=O)Nc2nccs2)cc1] | 31 | 2-[1-(4-Methoxy-benzyl)-3,4-dimethyl-5-oxo-2,5-dihydro-1H-pyrrol-2-yloxy]-N-thiazol-2-yl-acetamide |
| 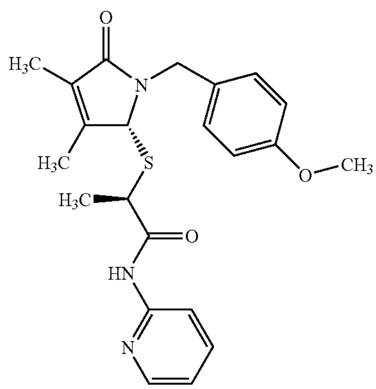 | 32 | 2-[1-(4-Methoxy-benzyl)-3,4-dimethyl-5-oxo-2,5-dihydro-1H-pyrrol-2-ylsulfanyl]-N-pyridin-2-yl-propionamide |
| 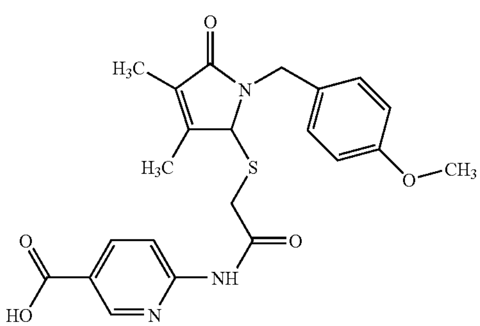 [SMILES: COc1ccc(CN2C(=O)C(C)=C(C)C2SCC(=O)Nc2ccc(C(=O)O)cn2)cc1] | 33 | 6-{2-[1-(4-Methoxy-benzyl)-3,4-dimethyl-5-oxo-2,5-dihydro-1H-pyrrol-2-ylsulfanyl]-acetylamino}-nicotinic acid |
| 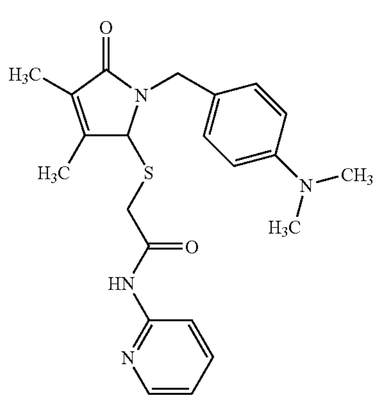 | 34 | 2-[1-(4-Dimethylamino-benzyl)-3,4-dimethyl-5-oxo-2,5-dihydro-1H-pyrrol-2-ylsulfanyl]-N-pyridin-2-yl-acetamide |

| STRUCTURE | COMPOUND # | NAME |
|---|---|---|
| 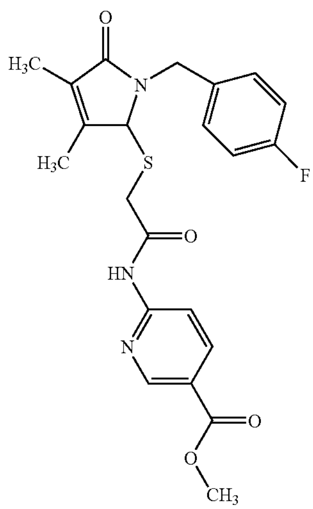 [SMILES: COC(=O)c1ccc(NC(=O)CSC2C(C)=C(C)C(=O)N2Cc2ccc(F)cc2)nc1] | 35 | 6-{2-[1-(4-Fluoro-benzyl)-3,4-dimethyl-5-oxo-2,5-dihydro-1H-pyrrol-2-ylsulfanyl]-acetylamino}-nicotinic acid methyl ester |
| 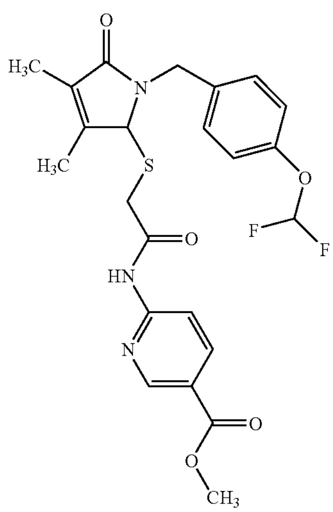 [SMILES: COC(=O)c1ccc(NC(=O)CSC2C(C)=C(C)C(=O)N2Cc2ccc(OC(F)F)cc2)nc1] | 36 | 6-{2-[1-(4-Difluoromethoxy-benzyl)-3,4-dimethyl-5-oxo-2,5-dihydro-1H-pyrrol-2-ylsulfanyl]-acetylamino}-nicotinic acid methyl ester |
| 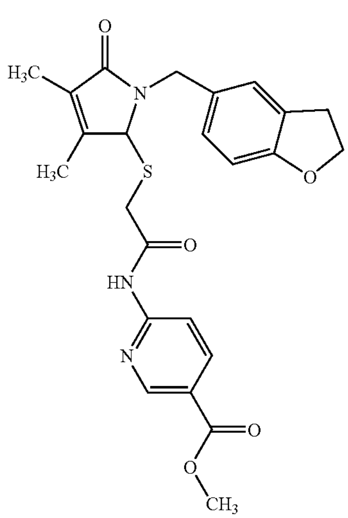 [SMILES: COC(=O)c1ccc(NC(=O)CSC2C(C)=C(C)C(=O)N2Cc2ccc3c(c2)CCO3)nc1] | 37 | 6-{2-[1-(2,3-Dihydro-benzofuran-5-ylmethyl)-3,4-dimethyl-5-oxo-2,5-dihydro-1H-pyrrol-2-ylsulfanyl]-acetylamino}-nicotinic acid methyl ester |

-continued

| STRUCTURE | COMPOUND # | NAME |
|---|---|---|
| 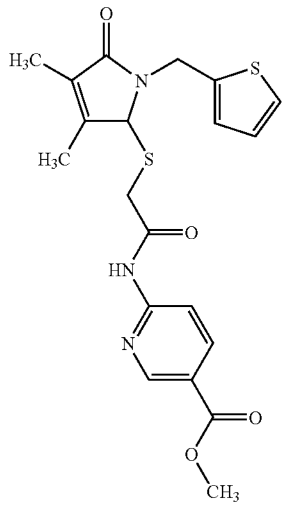 [SMILES: COC(=O)c1ccc(NC(=O)CSC2C(C)=C(C)C(=O)N2Cc2cccs2)nc1] | 38 | 6-[2-(3,4-Dimethyl-5-oxo-1-thiophen-2-ylmethyl-2,5-dihydro-1H-pyrrol-2-ylsulfanyl)-acetylamino]-nicotinic acid methyl ester |
| 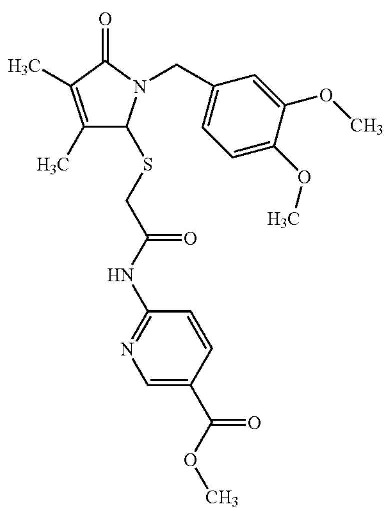 | 39 | 6-{2-[1-(3,4-Dimethoxy-benzyl)-3,4-dimethyl-5-oxo-2,5-dihydro-1H-pyrrol-2-ylsulfanyl]-acetylamino}-nicotinic acid methyl ester |
| 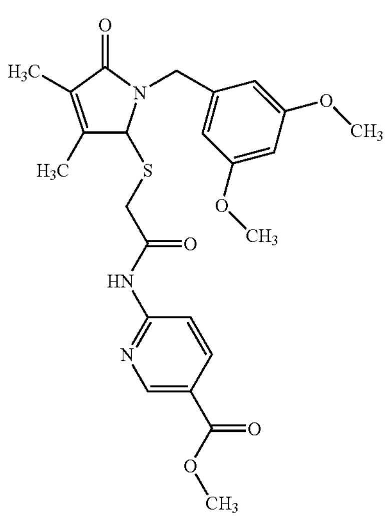 | 40 | 6-{2-[1-(3,5-Dimethoxy-benzyl)-3,4-dimethyl-5-oxo-2,5-dihydro-1H-pyrrol-2-ylsulfanyl]-acetylamino}-nicotinic acid methyl ester |

C) Synthesis

The invention provides methods of making the disclosed compounds according to traditional organic synthetic methods as well as matrix or combinatorial synthetic methods. Schemes I and II describe suggested synthetic routes. Using these Schemes, the guidelines below, and the examples, a person of skill in the art may develop analogous or similar methods for a given compound that is within the invention. These method are representative of the synthetic schemes, but are not to be construed as limiting the scope of the invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Examples 1 through 51 and Schemes I-IV. Compounds analogous to the target compounds of these examples can be made according to similar routes. The disclosed compounds are useful as pharmaceutical agents as described in the next section.

Abbreviations or acronyms useful herein include:
AIBN (2,2'-Azobisisobutyronitrile)
Boc (tert butyl carbamate)
BOP (Benzotriazol-1-yloxy)tris(dimethylamino)phosphonium hexfluorophosphate)
BuLi (butyllithium)
DIBAL-H (Diisobutylaluminum hydride)
DMAP (4-(dimethylamino)pyridine)
DME (Ethylene glycol dimethyl ether)
DMF (dimethylformamide)
DMPU (1,3-Dimethyl-3,4,5,6-tetrahydro-2(1H)-pyrimidinone)
DMSO (methyl sulfoxide)
EDC (N-(3-Dimethylaminopropyl)-N'-ethylcarbodiimide)
EDCI (1-(3-Dimethylaminopropyl)-3-ethylcarbodiimide hydrochloride)
EtOAc (ethyl acetate)
HATU (O-(7-Azabenzotriazol-1-yl)-N,N,N',N'-tetramethyluronium hexafluorophosphate)
HMPA (Hexamethylphosphoramide)
HOBt (1-Hydroxybenzotriazole monohydrate)
LCMS (high pressure liquid chroatography with mass spectrometer)
LDA (Lithium diisopropylamide)
LHMDS (lithium hexamethyl disilazide)
MOM (Methoxymethyl)
NaHMDS (sodium hexamethyl disilazide)
NaO$^t$Bu (sodium tert-butoxide)
NBS (N-Bromosuccinimide)
NMP (N-Methyl Pyrrolidinone)
Pd(Ph$_3$)$_4$ (Tetrakis(triphenylphosphine)palladium (0))
SPE (solid phase extraction)
TBTU (O-Benzotriazol-1-yl-N,N,N',N'-tetramethyluronium hexafluorophosphate)
TEMPO (2,2,6,6-tetramethyl-1-piperdinyloxy, free radical)
TFA (trifluoroacetic acid);
THF (tetrahydrofuran)
TLC (thin layer chromatography)
General Guidance Scheme 1

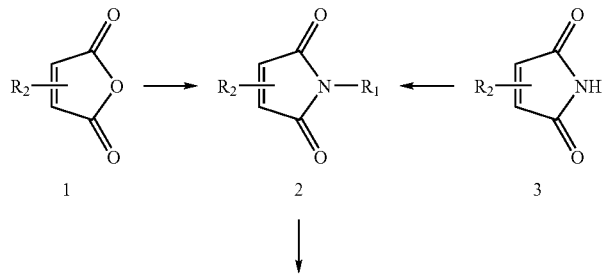

-continued

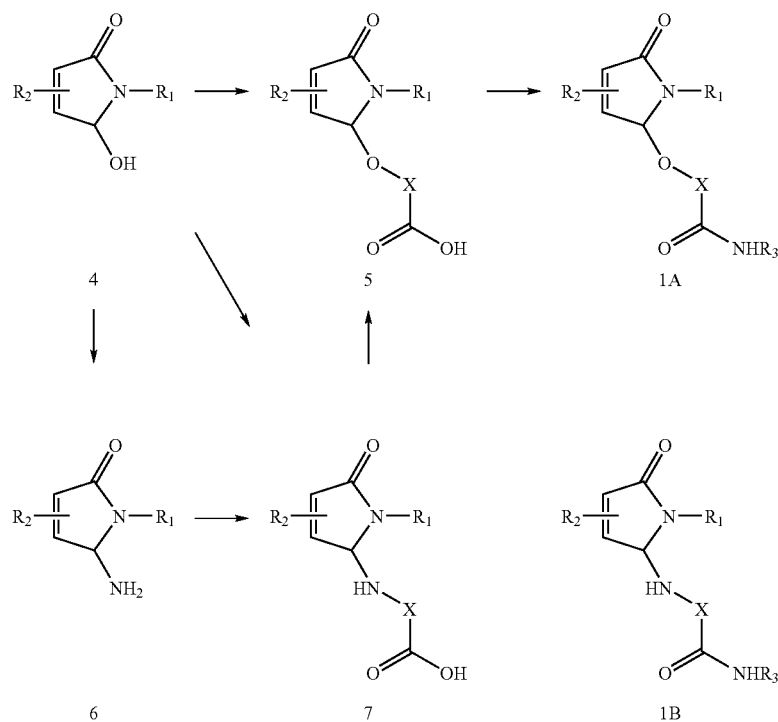

Compounds of Formula IA and IB wherein $R_3$ represents

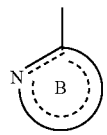

and $R_1$, $R_2$ and X are as described above, can be prepared as shown in Scheme I. In general, compounds of Formula 2 can be obtained from commercial sources or prepared by the addition of substituted primary amines to readily available substituted maleic anhydrides of general Formula 1 using acetic acid with or without a co-solvent like toluene and heating at temperatures between 80° C. and 100° C. Alternatively, compounds of Formula 3 can be N-alkylated by treatment with, for instance, substituted alkylbromide or alkyliodide in the presence of a base such as potassium carbonate or sodium carbonate in a solvent such as DMF or acetone at ambient to refluxing temperatures to provide compounds of Formula 2. The substituted maleimide 2 can then be reduced with sodium borohydride in an alcoholic solvent (such as EtOH) or lithium borohydride in THF at temperatures between −30° C. and 0° C. in the presence or absence of a Lewis acid such as cerium(III) chloride heptahydrate to provide compounds of Formula 4.

Compounds of general Formula 4 can be deprotonated with a base such as sodium hydride or potassium hydride then alkylated with an alkylating agent such as methyl bromoacetate or methyl 3-bromopropionate in a solvent such as dimethylformamide or tetrahydrofuran at temperatures ranging from 0° C. to reflux. The esters can then be saponified with potassium carbonate or sodium carbonate in aqueous methanol at 0° C. to ambient temperatures to provide the carboxylic acids of Formula 5. Compounds of Formula 5 can be converted to the acid chloride with reagents such as thionyl chloride or oxalyl chloride in a chlorinated solvent then subsequently treated with the selected substituted amine of the formula $R_3NH_2$ and a base such as pyridine, diisopropyethylamine or 2,6-lutidine at temperatures ranging from 0° C. to ambient to provide compounds of Formula IA. Alternatively, compounds of Formula 5 can be treated with coupling agents such as N-(3-Dimethylaminopropyl)-N'-ethylcarbodiimide (EDC) or O-(7-Azabenzotriazol-1-yl)-N,N,N',N'-tetramethyluronium hexafluorophosphate (HATU) and substituted amines of the formula $R_3NH_2$ in the presence of a base such as triethylamine or diisopropylethylamine in a chlorinated solvent such as dichloromethane at ambient temperature to afford compounds of Formula IA.

Compounds of Formula 4 can also be treated with phosphorus pentachloride as described by K. Nikitin and N. Andryukhova (Synthesis 2001, 89-92) followed by the addition of substituted or unsubstituted glycine methyl ester, β-alanine ethyl ester or ethyl 4-aminobutyrate to provide the intermediate substituted esters. Saponification of the intermediate esters as described above can provide the acid of Formula 7. In an alternative method, compounds of Formula 4 can be treated with thionyl chloride or phosphorus pentachloride followed by ammonium hydroxide in a chlorinated solvent at temperatures ranging from 0° C. to ambient to provide the primary amine of Formula 6. The amine of Formula 6 can then be alkylated by treatment with, for instance, ethyl bromoacetate or methyl bromoacetate and a base such as potassium or sodium carbonate in a solvent such as DMF or dioxane at temperatures between ambient and reflux. Saponification to the carboxylic acid of Formula 7 can be achieved as described above. Compounds of Formula 7 can be further treated with selected amines of the formula R$_3$NH$_2$ as previously described to provide compounds of Formula IB.

Scheme II

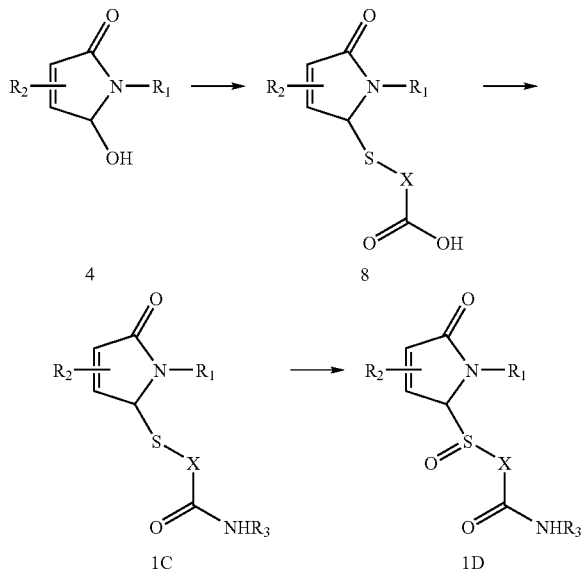

Compounds of general Formula IC and ID wherein R$_1$, R$_2$, R$_3$ and X are as described above can be prepared as shown in Scheme II. A compound of general Formula 4 can be converted to compounds of general Formula 8 by the addition of substituted or unsubstituted mercaptoacetic acids in the presence of p-toluenesulfonic acid or camphor sulfonic acid at temperatures between 0° C. and ambient. Compounds of Formula 8 can then be treated with selected substituted amines of the formula R$_3$NH$_2$ as previously described to provide compounds of Formula IC. Furthermore, compounds of Formula IC can be treated with an oxidizing agent such a meta-chloroperbenzoic acid in a chlorinated solvent such as dichloromethane or dichloroethane at temperatures ranging from 0° C. to ambient to provide compounds of Formula ID.

EXAMPLES

Example 1

6-{2-[1-(4-Methoxy-benzyl)-3,4-dimethyl-5-oxo-2, 5-dihydro-1H-pyrrol-2-ylsulfanyl]-acetylamino}-nicotinic acid methyl ester (Compound 1)

A. 1-(4-Methoxybenzyl)-3,4-dimethylpyrrole-2,5-dione 2,3-Dimethylmaleic anhydride (1 g, 7.9 mmol) and 4-methoxybenzylamine (1 mL, 7.9 mmol) were heated to reflux in 5 mL glacial acetic acid for 4.5 h. Solvent was evaporated. The residue was taken up in EtOAc and washed with sat'd aq NaHCO$_3$, water, and brine. The organic phase was dried (MgSO$_4$), filtered, and evaporated. The title compound was obtained as a solid and used without further purification (1.9 g, quant).

B. 5-Hydroxy-1-(4-methoxybenzyl)-3,4-dimethyl-1, 5-dihydropyrrol-2-one

The product from Part A (0.6 g, 2.5 mmol) and cerium chloride heptahydrate (910 mg, 2.5 mmol) were taken up in 5 mL THF and cooled to −30° C. LiBH$_4$ (1.2 mL, 2 M in THF) was added and stirring continued for 4.5 h as the temperature slowly rose to 0° C. Water was added, THF was evaporated, and the aqueous phase was washed with EtOAc. The organic phase was washed with brine, dried (MgSO$_4$), filtered, and evaporated. The title compound was obtained as a semi-solid and used without further purification (590 mg, 97%).

C. [1-(4-Methoxybenzyl)-3,4-dimethyl-5-oxo-2,5-dihydro-1H-pyrrol-2-ylsulfanyl]-acetic acid The product from Part B (500 mg, 2 mmol) was dissolved in 10 mL CH2Cl2 and cooled to 0° C. Mercaptoacetic acid (0.12 mL, 2 mmol) and camphorsulfonic acid (47 mg, 0.2 mmol) were added and the mixture was stirred for 1.5 h. Solvent was evaporated, the residue was taken up in EtOAc and water, and the aqueous phase was washed with EtOAc. The combined organics were washed with water and brine, then dried (MgSO$_4$), filtered, and evaporated. The title compound was obtained as an oil and used without further purification (770 mg, quant).

D. 6-{2-[1-(4-Methoxybenzyl)-3,4-dimethyl-5-oxo-2,5-dihydro-1H-pyrrol-2-ylsulfanyl]-acetylamino}-nicotinic acid methyl ester The product from Part C (350 mg, 1.1 mmol) was taken up in 5 mL CH$_2$Cl$_2$ and 2 drops DMF, then cooled to 0° C. Oxalyl chloride (0.65 mL, 2 M in CH$_2$Cl$_2$) and lutidine (0.08 mL, 0.65 mmol) were added and stirring continued for 3 h. 6-Aminonicotinic acid methyl ester (199 mg, 1.3 mmol) and lutidine (0.08 mL, 0.65 mmol) were added and stirring continued at 0° C. for 2.5 h. Water (10 mL) was added then CH$_2$Cl$_2$ and layers were separated. The organic layer was washed with brine, dried over MgSO$_4$, filtered and evaporated. The product was purified by silica gel chromatography. Recrystallization from MeOH gave the title compound as a white solid (62 mg, 12%). $^1$H NMR (300 MHz, CDCl$_3$) □ 8.89 (broad s, 1H); 8.88 (s, 1H); 8.32 (d, J=8.7 Hz, 1H); 8.22 (d, J=8.8 Hz, 1H); 7.22 (d, J=8.4 Hz, 2H); 6.84 (d, J=8.4 Hz, 2H); 5.10 (d, J=14.6 Hz, 1H); 4.62 (s, 1H); 4.16 (d, 14.6 Hz, 1H); 3.93 (s, 3H); 3.77 (s, 3H); 2.95 (s, 2H); 1.94 (s, 3H); 1.83 (s, 3H). MS: m/z (MH$^+$) 404.

Example 2

2[1-(4-Methoxy-benzyl)-3,4-dimethyl-5-oxo-2,5-dihydro-1H-pyrrol-2-ylsulfanyl]-N-thiazol-2-yl-acetamide (Compound 2)

The product from Example 1, Part C (350 mg, 1.1 mmol) and 2-aminothiazole (131 mg, 1.3 mmol) were converted to the title compound by the method described in Example 1, Part D (122 mg, 34%). $^1$H NMR (300 MHz, CDCl$_3$) δ 7.37 (d, J=3.5 Hz, 1H); 7.22 (d, J=8.8 Hz, 2H); 7.02 (d, J=3.6 Hz, 1H); 7.22 (d, J=8.5 Hz, 2H); 5.11 (d, J=14.6 Hz, 1H); 4.61 (s, 1H); 4.17 (d, 14.6 Hz, 1H); 3.76 (s, 3H); 3.06 (s, 2H); 1.93 (s, 3H); 1.79 (s, 3H). MS: m/z (MH$^+$) 404.

Example 3

2-[1-(4-Methoxy-benzyl)-5-oxo-4-phenyl-2,5-dihydro-1H-pyrrol-2-ylsulfanyl]-N-thiazol-2-yl-acetamide (Compound 3)

A. 1-(4-Methoxy-benzyl)-4-phenyl-pyrrole-2,5-dione

Phenylmaleic anhydride (2.4 g, 13.8 mmol) and 4-methoxybenzylamine (1.8 mL, 13.8 mmol) in 10 mL glacial acetic acid were heated in a 95° C. oil bath for 2 h. The mixture was cooled to room temperature, diluted with methanol and filtered to provide the title compound as a solid (3.2 g, 79%).

B. 5-Hydroxy-1-(4-methoxy-benzyl)-4-phenyl-1,5-dihydro-pyrrol-2-one

The product from Part A (1.01 g, 3.4 mmol) and cerium chloride heptahydrate (850 mg, 3.4 mmol) were taken up in EtOH/THF (150 mL/30 mL) and cooled to 0° C. NaBH$_4$ (130 mg, 3.4 mmol) was added portionwise and stirring continued for 20 minutes at 0° C. Ice water was added, EtOH was evaporated, and the aqueous phase was washed with EtOAc. The organic phase was washed with brine, dried (MgSO$_4$), filtered, and evaporated. The crude residue was chromatographed (CH$_2$Cl$_2$/EtOAc) to provide the title compound as a white solid. (0.669 mg, 66%).

C. [1-(4-Methoxy-benzyl)-5-oxo-4-phenyl-2,5-dihydro-1H-pyrrol-2-ylsulfanyl]-acetic acid The product from Part B (317 mg, 1.07 mmol) was dissolved in 3 mL CH$_2$Cl$_2$ and cooled to 0° C. Mercaptoacetic acid (0.17 mL, 1.07 mmol) and a catalytic amount of p-toluenesulfonic acid were added and the mixture was stirred for 2 h. Solvent was evaporated, the residue was taken up in EtOAc and water, and the aqueous phase was washed with EtOAc. The combined organics were washed with water and brine, then dried (MgSO$_4$), filtered, and evaporated. The title compound was obtained as a solid by trituration with Et$_2$O (273 mg, 69%).

D. 2-[1-(4-Methoxy-benzyl)-5-oxo-4-phenyl-2,5-dihydro-1H-pyrrol-2-ylsulfanyl]-N-thiazol-2-yl-acetamide The product from Part C (0.132 mg, 0.36 mmol) was taken up in 3 mL CH$_2$Cl$_2$ and 2 drops DMF, then cooled to 0° C. Oxalyl chloride (0.18 mL, 2 M in CH$_2$Cl$_2$) was slowly added. Stirring was continued at 0° C. for 1 hr and lutidine (0.02 mL, 0.17 mmol) was added. 2-aminothiazole (0.36 mg, 0.36 mmol) and lutidine (0.04 mL, 0.36 mmol) were added and stirring continued at 0° C. with slow warming up to room temperature over a 1 hr period. Water (10 mL) was added then CH$_2$Cl$_2$ and layers were separated. The organic layer was washed with brine, dried over MgSO$_4$, filtered and evaporated. Purification by chromatography (EtOAc/CH2Cl2) provided the title compound as a white solid from MeOH. $^1$H NMR (400 MHz, CDCl$_3$) □ 7.78 (m, 2H); 7.26 (m, 6H); 7.20 (s, 1H); 6.92 (s, 1H); 6.84 (d, J=8.4 Hz, 2H); 5.14 (d, J=15 Hz, 1H); 4.98 (s, 1H); 4.23 (d, 14.6 Hz, 1H); 3.78 (s, 3H); 3.15 (s, 2H). MS: m/z (MH$^+$) 452.

Example 4

6-{(2-[1-(4-Methoxy-benzyl)-5-oxo-3,4-diphenyl-2,5-dihydro-1H-pyrrol-2-ylsulfanyl]-acetylamino}-nicotinic acid methyl ester (Compound 4)

A. [1-(4-Methoxybenzyl)-5-oxo-3,4-diphenyl-2,5-dihydro-1H-pyrrol-2-ylsulfanyl]-acetic acid 3,4-Diphenylfuran-2,5-dione and 4-methoxybenzylamine were converted to the title compound by the method described in Example 1, Parts A, B, and C.

B. 6-{2-[1-(4-Methoxybenzyl)-5-oxo-3,4-diphenyl-2,5-dihydro-1H-pyrrol-2-ylsulfanyl]-acetylamino}-nicotinic acid methyl ester The product from Part A (150 mg, 0.3 mmol) and 6-aminonicotinic acid methyl ester (62 mg, 0.4 mmol) were converted to the title compound by the method described in Example 1, Part D (55 mg, 37%). $^1$H NMR (300 MHz, CDCl$_3$) δ 8.89 (broad s, 1H); 8.40 (s, 1H); 8.26 (d, J=8.5 Hz, 1H), 8.12 (d, J=8.8 Hz, 1H); 740-7.38 (m, 2H); 7.32-7.29 (m, 5H) 7.18-7.06 (m, 5H); 6.89 (d, J=8 Hz, 2H); 5.39 (s, 1H); 5.24 (d, J=14.6 Hz, 1H), 4.34 (d, 14.6 Hz, 1H); 3.92 (s, 3H); 3.79 (s, 3H); 3.09 (d, J=16 Hz, 1H); 2.99 (d, J=16 Hz, 1H). MS: m/z (MH$^+$) 580.

Example 5

2-[1-(4-Methoxy-benzyl)-3,4-dimethyl-5-oxo-2,5-dihydro-1H-pyrrol-2-ylsulfanyl]-N-pyridin-2-yl-acetamide (Compound 5)

The product from Example 1, Part C (200 mg, 0.6 mmol) was dissolved in 25 mL CH$_3$CN, HOBt (48 mg, 0.3 mmol) was added, and stirring continued for 1 h. 2-Aminopyridine (88 mg, 0.9 mmol), triethylamine (0.18 mL, 1.26 mmol), and HATU (250 mg, 0.66 mmol) were added and the mixture was stirred at room temperature for 2 h. Solvent was evaporated and the title compound was isolated as a white solid by silica gel chromatography (140 mg, 56%). $^1$H NMR (400 MHz, CDCl$_3$) δ 8.41 (br s, 1H), 8.29 (m, 1H), 8.13 (d, J=8 Hz, 1H), 7.70 (m, 1H), 7.22 (d, J=9 Hz, 2H), 7.06 (m, 1H), 6.83 (d, J=9 Hz, 2H), 5.07 (d, J=15 Hz, 1H), 4.62 (s, 1H), 4.15 (d, J=15 Hz, 1H), 3.77 (s, 3H), 2.90 (m, 2H), 1.95 (s, 3H), 1.84 (s, 3H). MS: m/z (MH$^+$) 398.

Example 6

2-[1-(4-Methoxy-benzyl)-3,4-dimethyl-5-oxo-2,5-dihydro-1H-pyrrol-2-ylsulfanyl]-N-pyrazin-2-yl-acetamide (Compound 6)

The product from Example 1, Part C (200 mg, 0.6 mmol) and 2-aminopyrazine (89 mg, 0.9 mmol) were reacted as described in Example 5. After evaporation of the reaction solvent the residue was partitioned between water and EtOAc, and the organic phase was washed with EtOAc. The combined organics were washed with brine, dried (Na$_2$SO$_4$), filtered, and evaporated. The title compound was obtained as a tan solid by silica gel chromatography. $^1$H NMR (400 MHz, CDCl$_3$) δ 9.48 (s, 1H), 8.70 (br s, 1H), 8.36 (d, J=2 Hz, 1H), 8.20 (m, 1H), 7.22 (d, J=8 Hz, 2H), 6.83 (d, J=8 Hz, 2H), 5.14 (d, J=14 Hz, 1H), 4.63 (s, 1H), 4.16 (d, J=14 Hz, 1H), 3.77 (s, 3H), 3.04 (d, J=16 Hz, 1H), 2.97 (d, J=16 Hz, 1H), 1.95 (s, 3H), 1.84 (s, 3H). MS: m/z (MH$^+$) 399.

Example 7

(2-{2-[1-(4-Methoxy-benzyl)-3,4-dimethyl-5-oxo-2,5-dihydro-1H-pyrrol-2-ylsulfanyl]-acetylamino}-thiazol-4-yl)-acetic acid ethyl ester (Compound 7)

The product from Example 1, Part C (160 mg, 0.5 mmol) and (2-aminothiazol-4-yl)-acetic acid ethyl ester (92 mg, 0.5 mmol) were reacted as described in Example 5. After evaporation of the reaction solvent the residue was partitioned between water and EtOAc, and the organic phase was washed with EtOAc. The combined organics were washed with brine, dried (Na$_2$SO$_4$), filtered, and evaporated. The title compound was obtained by silica gel chromatography (90 mg, 37%). $^1$H NMR (400 MHz, CDCl$_3$) δ 9.80 (br s, 1H), 7.22 (d, J=8 Hz, 2H), 6.83 (d, J=8 Hz, 2H), 6.80 (s, 1H), 5.19 (d, J=15 Hz, 1H), 4.60 (s, 1H), 4.15 (m, 3H), 3.77 (s, 3H), 3.61 (s, 3H), 3.06 (d, J=16 Hz, 1H), 2.98 (d, J=16 Hz, 1H), 1.90 (s, 3H), 1.81 (s, 3H). MS: m/z (MH$^+$) 490.

Example 8

N-(5-Chloro-pyridin-2-yl)-2-[1-(4-methoxy-benzyl)-3,4-dimethyl-5-oxo-2,5-dihydro-1H-pyrrol-2-ylsulfanyl]-acetamide (Compound 8)

The product from Example 1, Part C and 5-chloropyridin-2-ylamine were reacted as described in Example 5. After evaporation of the reaction solvent the residue was partitioned between water and EtOAc, and the organic phase was washed with EtOAc. The combined organics were washed with brine, dried (Na$_2$SO$_4$), filtered, and evaporated. The title compound was obtained by silica gel chromatography. $^1$H NMR (300 MHz, CDCl$_3$) δ 8.47 (br s, 1H), 8.22 (d, J=2 Hz, 1H), 8.12 (d, J=9 Hz, 1H), 7.66 (dd, J=9 Hz, 2 Hz, 1H), 7.21 (d, J=9 Hz, 2H), 6.83 (d, J=9 Hz, 2H), 5.07 (d, J=15 Hz, 1H), 4.62 (s, 1H), 4.13 (d, J=15 Hz, 1H), 3.77 (s, 3H), 2.91 (s, 2H), 1.94 (s, 3H), 1.84 (s, 3H). MS: m/z (MH$^+$) 432.

Example 9

2-[1-(4-Methoxy-benzyl)-3,4-dimethyl-5-oxo-2,5-dihydro-1H-pyrrol-2-ylsulfanyl]-N-(5-methyl-pyridin-2-yl)-acetamide (Compound 9)

The product from Example 1, Part C and 5-methylpyridin-2-ylamine were reacted as described in Example 5. After evaporation of the reaction solvent the residue was partitioned between water and EtOAc, and the organic phase was washed with EtOAc. The combined organics were washed with brine, dried (Na$_2$SO$_4$), filtered, and evaporated. The title compound was obtained by silica gel chromatography. $^1$H NMR (400 MHz, CDCl$_3$) δ 8.43 (br s, 1H), 8.09 (m, 1H), 8.02 (d, J=9 Hz, 1H), 7.51 (m, 1H), 7.21 (d, J=9 Hz, 2H), 6.83 (d, J=9 Hz, 2H), 5.07 (d, J=15 Hz, 1H), 4.61 (s, 1H), 4.14 (d, J=15 Hz, 1H), 3.77 (s, 3H), 2.89 (m, 2H), 2.30 (s, 3H), 1.95 (s, 3H), 1.83 (s, 3H). MS: m/z (MH$^+$) 412.

Example 10

2-[1-(2,4-Dimethoxy-benzyl)-3,4-dimethyl-5-oxo-2,5-dihydro-1H-pyrrol-2-ylsulfanyl]-N-pyridin-2-yl-acetamide (Compound 10)

A. [1-(2,4-Dimethoxy-benzyl)-3,4-dimethyl-5-oxo-2,5-dihydro-1H-pyrrol-2-ylsulfanyl]-acetic acid The title compound was prepared as described in Parts A-C of Example 1 substituting the 4-methoxybenzylamine with 2,4-dimethoxybenzylamine in Part A.

B. 2-[1-(2,4-Dimethoxy-benzyl)-3,4-dimethyl-5-oxo-2,5-dihydro-1H-pyrrol-2-ylsulfanyl]-N-pyridin-2-yl-acetamide The product from Part A (206 mg, 0.57 mmol) was dissolved in 25 mL CH$_3$CN, HOBt (44 mg, 0.3 mmol) was added, and stirring continued for 1 h. 2-Aminopyridine (54 mg, 0.57 mmol), triethylamine (0.1 mL, 0.63 mmol), and HATU (220 mg, 0.57 mmol) were added and the mixture was stirred at room temperature for 5 h. Water was then added and the acetonitrile removed under reduced pressure. The product was extracted with dichloromethane (3×). The combined organic extracts was washed with brine, dried over MgSO$_4$, filtered and evaporated in vauco. The crude product mixture was filtered through a SPE column, eluting further with CH$_2$Cl$_2$/EtOAc (9:1) to provide the product (25 mg, 10%). $^1$H NMR (400 MHz, CDCl$_3$) δ 8.59 (broad s, 1H); 8.28 (d, J=4 Hz, 1H); 8.15 (d, J=8.2 Hz, 1H); 7.73 (m, 1H); 7.21 (d, J=8.7 Hz, 1H); 7.07 (m, 1H); 6.42 (m, 2H); 4.87 (d, J=14.6 Hz, 1H); 4.75 (s, 1H); 4.42 (d, 14.9 Hz, 1H); 3.84 (s, 3H); 3.77 (s, 3H); 2.95 (s, 2H); 2.95 (s, 3H); 1.74 (s, 3H). MS: m/z (MH$^+$) 276.

Example 11

2-[1-(3,4-Dimethoxy-benzyl)-3,4-dimethyl-5-oxo-2,5-dihydro-1H-pyrrol-2-ylsulfanyl]-N-pyridin-2-yl-acetamide (Compound 11)

A. [1-(3,4-Dimethoxy-benzyl)-3,4-dimethyl-5-oxo-2,5-dihydro-1H-pyrrol-2-ylsulfanyl]-acetic acid The title compound was prepared as described in Parts A, B and C of Example 1 substituting the 4-methoxybenzylamine with 3,4-dimethoxybenzyl-amine in Part A.

B. 2-[1-(3,4-Dimethoxy-benzyl)-3,4-dimethyl-5-oxo-2,5-dihydro-1H-pyrrol-2-ylsulfanyl]-N-pyridin-2-yl-acetamide The product from Part A was treated as described in Example 5 to provide the title compound (30 mg, 15%). $^1$H NMR (300 MHz, CDCl$_3$) δ 8.50 (broad s, 1H); 8.28 (d, J=4 Hz, 1H); 8.15 (d, J=8.2 Hz, 1H); 7.73 (t, J=8.8 Hz, 1H); 7.07 (m, 1H); 6.86 6.77 (m, 3H); 5.11 (d, J=14.6 Hz, 1H); 4.62 (s, 1H); 4.15 (d, 14.9 Hz, 1H); 3.84 (s, 6H); 2.92 (s, 2H); 2.04 (s, 3H); 1.89 (s, 3H). MS: m/z (MH$^+$) 428.

Example 12

2-[1-(4-Fluoro-benzyl)-3,4-dimethyl-5-oxo-2,5-dihydro-1H-pyrrol-2-ylsulfanyl]-N-pyridin-2-yl-acetamide (Compound 12)

A. [1-(4-Fluoro-benzyl)-3,4-dimethyl-5-oxo-2,5-dihydro-1H-pyrrol-2-ylsulfanyl]-acetic acid The title compound was prepared as described in Parts A-C of Example 1 substituting the 4-methoxybenzylamine with 4-fluorobenzylamine in Part A.

B. 2-[1-(4-Fluoro-benzyl)-3,4-dimethyl-5-oxo-2,5-dihydro-1H-pyrrol-2-ylsulfanyl]-N-pyridin-2-yl-acetamide The product from Part A (0.2 g, 0.647 mmol) was treated as described in Example 5. Recrystallization from methanol provided pure product (82 mg, 41%). $^1$H NMR (400 MHz, CDCl$_3$) δ 8.72 (broad s, 1H); 8.25 (m, 1H); 8.15 (d, J=8.4 Hz, 1H); 7.73 (t, J=8.6 Hz, 1H); 7.27 (m, 2H); 7.06 (m, 1H); 6.99 (t, J=8.7 Hz, 2H); 5.14 (d, J=14.8 Hz, 1H); 4.62 (s, 1H); 4.22 (d, 14.8 Hz, 1H); 2.95 (s, 2H); 1.96 (s, 3H); 1.84 (s, 3H). MS: m/z (MH$^+$) 386.

Example 13

1-{2-[1-(4-Methoxybenzyl)-3,4-dimethyl-5-oxo-2,5-dihydro-1H-pyrrol-2-ylsulfanyl]-acetyl}-3-methylurea (Compound 13)

The product from Example 1, Part C (200 mg, 0.6 mmol) was dissolved in 3 mL chlorobenzene and 2 drops DMF, then cooled to 0° C. Oxalyl chloride (0.72 mL, 2 M in $CH_2Cl_2$) was added and the mixture was stirred for 1 h while the temperature rose to room temperature. Methyl urea (133 mg, 1.2 mmol) was added and the mixture was stirred at 70° C. for 10 min. pyridine (0.12 mL, 1.2 mmol) was added and the mixture was stirred at 70° C. for 0.5 h. The reaction solvent was evaporated and the product was purified by silica gel chromatography. Recrystallization from $CH_2Cl_2$/ether provided the title compound as a white solid (130 mg, 55%). $^1$H NMR (400 MHz, $CDCl_3$) δ 9.98 (br s, 1H), 8.21 (br s, 1H), 7.20 (d, J=8 Hz, 2H), 6.83 (d, J=8 Hz, 2H), 50.8 (d, J=15 Hz, 1H), 4.57 (s, 1H), 4.14 (d, J=15 Hz, 1H), 3.77 (s, 3H), 2.89 (m, 5H), 1.95 (s, 3H), 1.84 (s, 3H). MS: m/z ($MH^+$) 378.

Example 14

(2-{2-[1-(4-Methoxy-benzyl)-3,4-dimethyl-5-oxo-2,5-dihydro-1H-pyrrol-2-ylsulfanyl]-acetylamino}-thiazol-4-yl)-acetic acid (Compound 14)

The product from Example 7 (100 mg, 0.2 mmol) was dissolved in 4 mL THF and cooled to 0° C. LiOH (56 mg, 0.8 mmol) in 4 mL water was added dropwise. The mixture was warmed to room temperature and stirred for 3 h. The mixture was cooled to 0° C. and diluted with 10 mL EtOAc. 2N aq HCl was added until the mixture reached pH1. The aqueous phase was washed with EtOAc. The combined organics were washed with water, dried ($Na_2SO_4$), filtered, and evaporated. Recrystallization fro ether/hexane provided the title compound as a tan powder (60 mg, 63%). $^1$H NMR (400 MHz, $CDCl_3$) δ 7.17 (d, J=9 Hz, 2H), 6.81 (m, 3H), 5.02 (d, J=15 Hz, 1H), 4.55 (s, 1H), 4.15 (d, J=15 Hz, 1H), 3.77 (s, 3H), 3.72 (s, 2H), 3.11 (d, J=15 Hz, 1H), 2.96 (d, J=15 Hz, 1H), 1.89 (s, 3H), 1.76 (s, 3H). MS: m/z ($MH^+$) 462.

Example 15

2-[1-(4-Methoxy-benzyl)-4-methyl-5-oxo-2,5-dihydro-1H-pyrrol-2-ylsulfanyl]-N-pyridin-2-yl-acetamide (Compound 15)

A.
1-(4-Methoxy-benzyl)-3-methyl-pyrrole-2,5-dione

3-Methylmaleic anhydride (10 g, 89.2 mmol) and 4-methoxybenzylamine (11.6 mL, 89.2 mmol) were heated to 100° C. in 35 mL glacial acetic acid for 5 h. Solvent was evaporated. The residue was taken up in EtOAc and washed with sat'd aq $NaHCO_3$, water, and brine. The organic phase was dried ($MgSO_4$), filtered, and evaporated. The title compound was obtained as a solid and used without further purification (18.75 g, quant).

B. 5-Hydroxy-1-(4-methoxy-benzyl)-3-methyl-1,5-dihydro-pyrrol-2-one and 5-Hydroxy-1-(4-methoxy-benzyl)-4-methyl-1,5-dihydro-pyrrol-2-one The product from Part A (1.5 g, 6.5 mmol) and cerium chloride heptahydrate (2.4 g, 6.5 mmol) were taken up in 25 mL THF and stirred at room temperature for 20 minutes. The mixture was then cooled to −30° C., $LiBH_4$ (1.2 mL, 2 M in THF) was added and stirring continued for 4.5 h as the temperature slowly rose to 0° C. Water was added, THF was evaporated, and the aqueous phase was washed with EtOAc (3×). The organic phase was washed with brine, dried ($MgSO_4$), filtered, and evaporated. The residue was chromatographed to provide the title compounds; 3-methyl regioisomer (0.416 g) and 4-methyl regioisomer (0.899 g).

C. [1-(4-Methoxybenzyl)-3-methyl-5-oxo-2,5-dihydro-1H-pyrrol-2-ylsulfanyl]-acetic acid The 3-methyl regioisomer from Part B (0.2 g, 0.86 mmol) was dissolved in 10 mL $CH_2Cl_2$ and cooled to 0° C. Mercaptoacetic acid (0.06 mL, 0.86 mmol) and camphorsulfonic acid (20 mg, 0.086 mmol) were added and the mixture was stirred for 1.5 h. Solvent was evaporated, the residue was taken up in EtOAc and water, and the aqueous phase was washed with EtOAc. The combined organics were washed with water and brine, then dried ($MgSO_4$), filtered, and evaporated. The title compound was obtained as an oil and used without further purification (300 mg, quant).

D. 6-{2-[1-(4-Methoxybenzyl)-3-methyl-5-oxo-2,5-dihydro-1H-pyrrol-2-ylsulfanyl]-acetylamino}-nicotinic acid methyl ester The product from part C (250 mg, 0.81) was treated as described in Example 5. Recrystallization from MeOH provided the title compound (89 mg, 35%). $^1$H NMR (400 MHz, $CDCl_3$) δ 8.75 (broad s, 1H); 8.28 (m, 1H); 8.15 (d, J=8.1 Hz, 1H); 7.73 (t, J=8.8 Hz, 1H); 7.22 (d, J=8.7 Hz, 2H); 7.07 (m, 1H); 6.84 (d, J=8.7 Hz, 2H); 6.59 (s, 1H); 5.09 (d, J=14.6 Hz, 1H); 4.82 (s, 1H); 4.17 (d, 14.9 Hz, 1H); 3.77 (s, 3H); 3.07 (d, J=16.3 Hz, 1H); 2.97 (d, J=16.3 Hz, 1H); 1.89 (s, 3H). MS: m/z ($MH^+$) 384.

Example 16

2-[1-(4-Difluoromethoxy-benzyl)-3,4-dimethyl-5-oxo-2,5-dihydro-1H-pyrrol-2-ylsulfanyl]-N-pyridin-2-yl-acetamide (Compound 16)

A. [1-(4-Difluoromethoxy-benzyl)-3,4-dimethyl-5-oxo-2,5-dihydro-1H-pyrrol-2-ylsulfanyl]-acetic acid The title compound was prepared as described in Parts A-C of Example 1 substituting the 4-methoxybenzylamine with 4-difluoromethoxybenzylamine in Part A.

B. 2-[1-(4-Difluoromethoxy-benzyl)-3,4-dimethyl-5-oxo-2,5-dihydro-1H-pyrrol-2-ylsulfanyl]-N-pyridin-2-yl-acetamide The product from Part A (0.35 g, 0.98 mmol) was dissolved in 5 mL of $CH_2Cl_2$ and HATU (0.56 g, 1.47 mmol) was added. The mixture was stirred at room temperature for 10 minutes and 2-aminopyridine (0.14 g, 1.47 mmol) and triethylamine (0.41 mL, 2.94 mmol) were added and the mixture stirred at room temperature overnight. Water was added. Dichloromethane was added and layers were separated. The $CH_2Cl_2$ layer was washed with $H_2O$ (2×), brine (1×) then dried over $MgSO_4$. Solvents were removed under reduced pressure and the product triturated with methanol. The solid product was isolated by filtration rinsing several times with MeOH to provide the title compound (0.33 g, 78%). $^1$H NMR (400

MHz, CDCl₃) δ 8.50 (broad s, 1H); 8.28 (m, 1H); 8.14 (d, J=8.3 Hz, 1H); 7.73 (t, J=8.5 Hz, 1H); 7.29-7.26 (m, 2H); 7.08-7.04 (m, 3H); 6.47 (s, 1H); 6.59 (s, 1H); 5.13 (d, J=14.8 Hz, 1H); 4.63 (s, 1H); 4.23 (d, 14.9 Hz, 1H); 2.92 (s, 2H); 1.97 (s, 3H); 1.85 (s, 3H). MS: m/z (MH⁺) 434.

Example 17

N-(5-Cyano-pyridin-2-yl)-2-[1-(4-methoxy-benzyl)-3,4-dimethyl-5-oxo-2,5-dihydro-1H-pyrrol-2-ylsulfanyl]-acetamide (Compound 17)

The product from Example 1, Part C (160 mg, 0.5 mmol) and 6-aminonicotinonitrile (89 mg, 0.75 mmol) were reacted as described in Example 5. After evaporation of the reaction solvent the residue was partitioned between water and EtOAc, the aqueous phase was washed with EtOAc. The combined organics were washed with brine, dried (Na₂SO₄), filtered, and evaporated. The title compound was obtained by silica gel chromatography (30 mg, 14%). ¹H NMR (400 MHz, CDCl₃) δ 8.84 (br s, 1H), 8.55 (d, J=2 Hz, 1H), 8.30 (d, J=9 Hz, 1H), 7.95 (dd, J=9 Hz, 2 Hz, 1H), 7.21 (d, J=9 Hz, 2H), 6.83 (d, J=9 Hz, 2H), 5.07 (d, J=15 Hz, 1H), 4.63 (s, 1H), 4.12 (d, J=15 Hz, 1H), 3.77 (s, 3H), 2.96 (m, 2H), 1.94 (s, 3H), 1.84 (s, 3H). MS: m/z (MNa⁺) 445.

Example 18

6-{(2-[1-(4-Methoxy-benzyl)-3,4-dimethyl-5-oxo-2,5-dihydro-1H-pyrrol-2-ylsulfanyl]-acetylamino}-nicotinamide (Compound 18)

The product from Example 1, Part C (160 mg, 0.5 mmol) and 6-aminonicotinamide (103 mg, 0.75 mmol) were reacted as described in Example 5. After evaporation of the reaction solvent the residue was partitioned between water and EtOAc, and the aqueous phase was washed with EtOAc. The combined organics were washed with brine, dried (Na₂SO₄), filtered, and evaporated. The title compound was obtained by silica gel chromatography (10 mg, 5%). ¹H NMR (300 MHz, CDCl₃) δ 8.76 (d, J=2 Hz, 1H), 8.71 (br s, 1H), 8.22 (d, J=9 Hz, 1H), 8.13 (dd, J=9 Hz, 2 Hz, 1H), 7.20 (d, J=9 Hz, 2H), 6.83 (d, J=9 Hz, 2H), 5.05 (d, J=15 Hz, 1H), 4.63 (s, 1H), 4.13 (d, J=15 Hz, 1H), 3.77 (s, 3H), 2.94 (s, 2H), 1.95 (s, 3H), 1.83 (s, 3H). MS: m/z (MH⁺) 441.

Example 19

2-[1-(4-Methoxy-benzyl)-3-methyl-5-oxo-2,5-dihydro-1H-pyrrol-2-ylsulfanyl]-N-pyridin-2-yl-acetamide (Compound 19)

A. [1-(4-Methoxy-benzyl)-3-methyl-5-oxo-2,5-dihydro-1H-pyrrol-2-ylsulfanyl]-acetic acid The 4-methyl regioisomer obtained in Part B of Example 15 was treated as described in Part C of Example 15.

B. 2-[1-(4-Methoxy-benzyl)-3-methyl-5-oxo-2,5-dihydro-1H-pyrrol-2-ylsulfanyl]-N-pyridin-2-yl-acetamide The product of Part A (0.36 g, 1.17 mmol) was treated as described in Part B of Example 16 to provide the title compound (60 mg, 13%). ¹H NMR (400 MHz, CDCl₃) δ 8.56 (broad s, 1H); 8.28 (m, 1H); 8.15 (d, J=8.1 Hz, 1H); 7.73 (t, J=8.8 Hz, 1H); 7.23 (d, J=8.7 Hz, 2H); 7.08-7.05 (m, 1H); 6.84 (d, J=8.7 Hz, 2H); 6.00 (s, 1H); 5.07 (d, J=15 Hz, 1H), 4.70 (s, 1H); 4.14 (d, 15 Hz, 1H); 3.77 (s, 3H); 2.98 (s, 2H); 2.07 (s, 3H). MS: m/z (MH⁺) 384.

Example 20

2-[1-(2,3-Dihydro-benzofuran-5-ylmethyl)-3,4-dimethyl-5-oxo-2,5-dihydro-1H-pyrrol-2-ylsulfanyl]-N-pyridin-2-yl-acetamide (Compound 20)

A. [1-(2,3-Dihydro-benzofuran-5-ylmethyl)-3,4-dimethyl-5-oxo-2,5-dihydro-1H-pyrrol-2-ylsulfanyl]-acetic acid The title compound was prepared as described in Parts A-C of Example 1 substituting the 4-methoxybenzylamine with (2,3-Dihydro-benzofuran-5-yl)-methylamine in Part A.

B. 2-[1-(2,3-Dihydro-benzofuran-5-ylmethyl)-3,4-dimethyl-5-oxo-2,5-dihydro-1H-pyrrol-2-ylsulfanyl]-N-pyridin-2-yl-acetamide The compound prepared in Part A (0.35 g, 1.05 mmol) was treated as described in Part B of Example 16 to provide the title compound (0.25 g, 60%). ¹H NMR (400 MHz, CDCl₃) δ 8.61 (broad s, 1H); 8.27 (m, 1H); 8.15 (d, J=7.9 Hz, 1H); 7.73 (m, 1H); 7.13 (s, 1H); 7.07-7.02 (m, 2H); 6.70 (d, J=8.0 Hz, 2H); 5.09 (d, J=15 Hz, 1H); 4.64 (s, 1H); 4.55 (t, J=8.8 Hz, 2H); 4.13 (d, J=15 Hz, 1H); 3.17 (t, J=8.7 Hz, 2H); 2.94 (s, 2H); 1.95 (s, 3H); 1.83 (s, 3H). MS: m/z (MH⁺) 410.

Example 21

2-[1-(4-Methoxy-benzyl)-3,4-dimethyl-5-oxo-2,5-dihydro-1H-pyrrol-2-ylsulfanyl]-N-(4-methyl-pyridin-2-yl)-acetamide (Compound 21)

The product from Example 1, Part C (0.3 g, 0.93 mmol) and 2-amino-4-picoline (0.151 g, 1.4 mmol) were converted to the title compound by the method described in Part B of Example 16 (0.223 g, 58%). ¹H NMR (300 MHz, CDCl₃) δ 8.28 (broad s, 1H); 7.92 (d, J=8 Hz, 1H); 7.60 (t, J=7.8 Hz, 1H); 7.23 (d, J=8.6 Hz, 2H); 6.88 (d, J=7.4 Hz, 1H); 6.84 (d, J=8.5 Hz, 2H); 5.11 (d, J=15 Hz, 1H), 4.61 (s, 1H); 4.16 (d, 15 Hz, 1H); 3.76 (s, 3H); 2.89 (s, 2H); 2.44 (s, 3H); 1.94 (s, 3H); 1.84 (s, 3H). MS: m/z (MH⁺) 412.

Example 22

N-(4-Ethyl-pyridin-2-yl)-2-[1-(4-methoxy-benzyl)-3,4-dimethyl-5-oxo-2,5-dihydro-1H-pyrrol-2-ylsulfanyl]-acetamide (Compound 22)

The product from Example 1, Part C (0.3 g, 0.93 mmol) and 2-amino-4-ethylpyridine (0.171 g, 1.4 mmol) were converted to the title compound by the method described in Part B of Example 16 (121 mg, 30%). ¹H NMR (300 MHz, CDCl₃) δ 8.53 (broad s, 1H); 8.15 (d, J=5.16 Hz, 1H); 7.99 (s, 1H); 7.23 (d, J=8.4 Hz, 2H); 6.92 (m, 1H); 6.84 (d, J=8.5 Hz, 2H); 5.11 (d, J=15 Hz, 1H); 4.61 (s, 1H); 4.16 (d, 15 Hz, 1H); 3.77 (s, 3H); 2.90 (s, 2H); 2.67 (q, J=7.4 Hz, 2H); 1.95 (s, 3H); 1.84 (s, 3H); 1.27 (t, J=7.6 Hz, 3H). MS: m/z (MH⁺) 426.

Example 23

2-[1-(4-Methoxy-benzyl)-3,4-dimethyl-5-oxo-2,5-dihydro-1H-pyrrol-2-ylsulfanyl]-N-(6-methyl-pyridin-2-yl)-acetamide (Compound 23)

The product from Example 1, Part C (0.3 g, 0.93 mmol) and 2-amino-6-picoline (0.152 g, 1.4 mmol) were converted to the title compound by the method described in Part B of Example 16 (271 mg, 70%). $^1$H NMR (300 MHz, CDCl$_3$) δ 8.50 (broad s, 1H); 8.12 (d, J=5 Hz, 1H); 7.96 (s, 1H); 7.20 (d, J=8.4 Hz, 2H); 6.88 (d, J=5 Hz, 1H); 6.84 (d, J=8.4 Hz, 2H); 5.10 (d, J=14.6 Hz, 1H), 4.61 (s, 1H); 4.16 (d, 14.9 Hz, 1H); 3.76 (s, 3H); 2.90 (s, 2H); 2.36 (s, 3H); 1.95 (s, 3H); 1.84 (s, 3H). MS: m/z (MH$^+$) 412.

Example 24

2-(3,4-Dimethyl-5-oxo-1-thiophen-2-ylmethyl-2,5-dihydro-1H-pyrrol-2-ylsulfanyl)-N-pyridin-2-yl-acetamide (Compound 24)

A. (3,4-Dimethyl-5-oxo-1-thiophen-2-ylmethyl-2,5-dihydro-1H-pyrrol-2-ylsulfanyl)-acetic acid The title compound was prepared by the method described in Parts A, B and C of Example 1 substituting the 4-methoxybenzylamine with thiophen-2-yl-methylamine in Part A.

B. 2-(3,4-Dimethyl-5-oxo-1-thiophen-2-yl methyl-2,5-dihydro-1H-pyrrol-2-ylsulfanyl)-N-pyridin-2-yl-acetamide The product of Part A (0.5 g, 1.68 mmol) was treated by the method described in Part B of Example 16 to provide the title compound (84.5 mg, 13%). $^1$H NMR (400 MHz, CDCl$_3$) δ 8.75 (broad s, 1H); 8.26 (m, 1H); 8.15 (d, J=8.3 Hz, 1H); 7.73 (t, J=8.5 Hz, 1H); 7.21 (d, J=5 Hz, 1H); 7.07-7.01 (m, 2H); 6.94 (m, 1H); 5.26 (d, J=15 Hz, 1H); 4.76 (s, 1H); 4.50 (d, 15 Hz, 1H); 2.96 (s, 2H); 1.96 (s, 3H); 1.83 (s, 3H). MS: m/z (MH$^+$) 374.

Example 25

2-[1-(4-Isopropyl-benzyl)-3,4-dimethyl-5-oxo-2,5-dihydro-1H-pyrrol-2-ylsulfanyl]-N-pyridin-2-yl-acetamide (Compound 25)

A. [1-(4-Isopropyl-benzyl)-3,4-dimethyl-5-oxo-2,5-dihydro-1H-pyrrol-2-ylsulfanyl]-acetic acid The title compound was prepared by the method described in Parts A, B and C of Example 1 substituting the 4-methoxybenzylamine with 4-isopropylbenzylamine in Part A.

B. 2-[1-(4-Isopropyl-benzyl)-3,4-dimethyl-5-oxo-2,5-dihydro-1H-pyrrol-2-ylsulfanyl]-N-pyridin-2-yl-acetamide The product of Part A (0.5 g, 1.5 mmol) was treated by the method described in Part B of Example 16 to provide the title compound (65.3 mg, 10%). $^1$H NMR (400 MHz, CDCl$_3$) □ 8.89 (broad s, 1H); 8.25 (m, 1H), 8.15 (d, J=8.4 Hz, 1H); 7.73 (t, J=8.5 Hz, 1H); 7.21 (d, J=8 Hz, 2H); 7.16 (d, J=8 Hz, 2H); 7.06 (m, 1H); 5.17 (d, J=15 Hz, 1H), 4.64 (s, 1H); 4.18 (d, J=15 Hz, 1H); 2.97 (s, 2H); 2.88-2.85 (m, 1H); 1.95 (s, 3H); 1.83 (s, 3H); 1.22 (s, 3H); 1.20 (s, 3H). MS: m/z (MH$^+$) 410.

Example 26

2-[1-(4-Ethyl-benzyl)-3,4-dimethyl-5-oxo-2,5-dihydro-1H-pyrrol-2-ylsulfanyl]-N-pyridin-2-yl-acetamide (Compound 26)

A. [1-(4-Ethyl-benzyl)-3,4-dimethyl-5-oxo-2,5-dihydro-1H-pyrrol-2-ylsulfanyl]-acetic acid The title compound was prepared by the method described in Parts A, B and C of Example 1 substituting the 4-methoxybenzylamine with 4-ethylbenzylamine in Part A.

B. 2-[1-(4-ethyl-benzyl)-3,4-dimethyl-5-oxo-2,5-dihydro-1H-pyrrol-2-ylsulfanyl]-N-pyridin-2-yl-acetamide The product of Part A (0.5 g, 1.57 mmol) was treated by the method described in Part B of Example 16 to provide the title compound (79.8 mg, 13%). $^1$H NMR (400 MHz, CDCl$_3$) δ 8.89 (broad s, 1H); 8.25 (m, 1H), 8.15 (d, J=8.4 Hz, 1H); 7.73 (t, J=8.5 Hz, 1H); 7.26 (d, J=8 Hz, 2H); 7.18 (d, J=8 Hz, 2H); 7.06 (m, 1H); 5.17 (d, J=15 Hz, 1H), 4.63 (s, 1H); 4.19 (d, J=15 Hz, 1H); 2.97 (s, 2H); 2.63 (q, J=7.6 Hz, 2H); 1.94 (s, 3H); 1.83 (s, 3H); 1.19 (t, J=7.6 Hz, 3H). MS: m/z (MH$^+$) 396.

Example 27

6-{2-[1-(4-Methoxy-benzyl)-3,4-dimethyl-5-oxo-2,5-dihydro-1H-pyrrol-2-yloxy]-acetylamino}-nicotinic acid methyl ester (Compound 27)

A. [1-(4-Methoxybenzyl)-3,4-dimethyl-5-oxo-2,5-dihydro-1H-pyrrol-2-yloxy]-acetic acid methyl ester The product from Example 1, Part B (400 mg, 1.6 mmol) in 15 mL THF was cooled to 0° C. under N2. Sodium hydride (58 mg, 2.4 mmol) was added in two portions and stirring continued for 0.5 h. Ethyl bromoacetate (400 mg, 2.4 mmol) in 5 mL THF was added dropwise over 5 min, and stirring continued at room temperature for 24 h. Solvent was evaporated, the mixture was cooled to 0° C., EtOAc was added, followed by cold water. The aqueous phase was washed with EtOAc. The combined organics were dried (Na$_2$SO$_4$), filtered, and evaporated. The title compound was isolated as an oil and used without further purification (450 mg, 83%).

B. [1-(4-Methoxybenzyl)-3,4-dimethyl-5-oxo-2,5-dihydro-1H-pyrrol-2-yloxy]-acetic acid The product from Part C (100 mg, 0.3 mmol) was stirred with LiOH (81 mg, 1.2 mmol) in 5 mL THF and 5 mL water. After 4 h at room temperature the mixture was neutralized with 1 N aq. HCl, then washed with EtOAc. The organic phase was dried (Na$_2$SO$_4$), filtered, and evaporated. The title compound was used without further purification (90 mg, 98%).

C. 6-{2-[1-(4-Methoxybenzyl)-3,4-dimethyl-5-oxo-2,5-dihydro-1H-pyrrol-2-yloxy]-acetylamino}-nicotinic acid methyl ester The product from Part B (90 mg, 0.3 mmol) and 6-aminonicotinic acid methyl ester (67 mg, 0.44 mmol) were reacted as described in Example 5. After evaporation of the reaction solvent the residue was partitioned between water and EtOAc, and the organic phase was washed with EtOAc. The combined organics were washed with brine, dried ($Na_2SO_4$), filtered, and evaporated. The title compound was obtained as a white solid by silica gel chromatography (50 mg, 38%). $^1$H NMR (400 MHz, $CDCl_3$) δ 8.95 (s, 1H), 8.86 (br s, 1H), 8.30 (m, 1H), 8.24 (d, J=9 Hz, 1H), 7.22 (d, J=8 Hz, 2H), 6.77 (d, J=8 Hz, 2H), 5.19 (s, 1H), 4.69 (d, J=15 Hz, 1H), 4.28 (d, J=15 Hz, 1H), 3.95 (s, 3H), 3.67 (m, 4H), 3.59 (d, J=15 Hz, 1H), 1.87 (s, 6H). MS: m/z ($MH^+$) 440.

Example 28

2-[1-(4-Methoxy-benzyl)-3,4-dimethyl-5-oxo-2,5-dihydro-1H-pyrrol-2-yloxy]-N-(5-methyl-pyridin-2-yl)-acetamide (Compound 28)

The product from Example 27, Part B (100 mg, 0.3 mmol) and 5-methylpyridin-2-ylamine (71 mg, 0.66 mmol) were reacted as described in Example 5. After evaporation of the reaction solvent the residue was partitioned between water and EtOAc, and the organic phase was washed with EtOAc. The combined organics were washed with brine, dried ($Na_2SO_4$), filtered, and evaporated. The title compound was obtained as a white solid by silica gel chromatography. $^1$H NMR (300 MHz, $CDCl_3$) δ 8.68 (br s, 1H), 8.14 (s, 1H), 8.07 (d, J=8 Hz, 1H), 7.53 (m, 1H), 7.22 (d, J=9 Hz, 2H), 6.79 (d, J=9 Hz, 2H), 5.16 (s, 1H), 4.75 (d, J=15 Hz, 1H), 4.21 (d, J=15 Hz, 1H), 3.70 (s, 3H), 3.68 (d, J=15 Hz, 1H), 3.58 (d, J=15 Hz, 1H), 2.32 (s, 3H), 1.86 (s, 6H). MS: m/z ($MH^+$) 396.

Example 29

2-[1-(3,5-Dimethoxy-benzyl)-3,4-dimethyl-5-oxo-2,5-dihydro-1H-pyrrol-2-ylsulfanyl]-N-pyridin-2-yl-acetamide (Compound 29)

A. [1-(3,5-dimethoxy-benzyl)-3,4-dimethyl-5-oxo-2,5-dihydro-1H-pyrrol-2-ylsulfanyl]-acetic acid The title compound was prepared by the method described in Parts A, B and C of Example 21 substituting the 4-methoxybenzylamine with 3,5-dimethoxybenzylamine in Part A.

B. 2-[1-(3,5-dimethoxy-benzyl)-3,4-dimethyl-5-oxo-2,5-dihydro-1H-pyrrol-2-ylsulfanyl]-N-pyridin-2-yl-acetamide The product of Part A (0.5 g, 1.42 mmol) was treated by the method described in Part B of Example 16 to provide the title compound (0.42 g, 69%). $^1$H NMR (400 MHz, $CDCl_3$) δ 8.70 (broad s, 1H); 8.27 (m, 1H), 8.15 (d, J=8.4 Hz, 1H); 7.73 (t, J=8.5 Hz, 1H); 7.07-7.04 (m, 1H); 6.42 (s, 2H); 6.35 (s, 1H); 5.14 (d, J=15 Hz, 1H), 4.67 (s, 1H); 4.13 (d, J=15 Hz, 1H); 3.76 (s, 6H); 2.95 (s, 2H); 1.96 (s, 3H); 1.83 (s, 3H); MS: m/z ($MH^+$) 428.

Example 30

2-[1-(4-Methoxy-benzyl)-3,4-dimethyl-5-oxo-2,5-dihydro-1H-pyrrol-2-yloxy]-N-pyridin-2-yl-acetamide (Compound 30)

The product from Example 27, Part B (90 mg, 0.3 mmol) and 2-aminopyridine (42 mg, 0.45 mmol) were reacted as described in Example 5. After evaporation of the reaction solvent the residue was partitioned between water and EtOAc, and the organic phase was washed with EtOAc. The combined organics were washed with brine, dried ($Na_2SO_4$), filtered, and evaporated. The title compound was obtained as a white solid by silica gel chromatography (40 mg, 35%). $^1$H NMR (300 MHz, $CDCl_3$) δ 8.72 (br s, 1H), 8.33 (d, J=4 Hz, 1H), 8.18 (d, J=8 Hz, 1H), 7.72 (m, 1H), 7.23 (d, J=9 Hz, 2H), 7.08 (m, 1H), 6.79 (d, J=9 Hz, 2H), 5.17 (s, 1H), 4.73 (d, J=15 Hz, 1H), 4.23 (d, J=15 Hz, 1H), 3.70 (d, J=15 Hz, 1H), 3.69 (s, 3H), 3.59 (d, J=15 Hz, 1H), 1.87 (s, 6H). MS: m/z ($MH^+$) 382.

Example 31

2-[1-(4-Methoxy-benzyl)-3,4-dimethyl-5-oxo-2,5-dihydro-1H-pyrrol-2-yloxy]-N-thiazol-2-yl-acetamide (Compound 31)

The product from Example 27, Part B (60 mg, 0.2 mmol) and 2-thiazole (30 mg, 0.3 mmol) were reacted as described in Example 5. After evaporation of the reaction solvent the residue was partitioned between water and EtOAc, and the organic phase was washed with EtOAc. The combined organics were washed with brine, dried ($Na_2SO_4$), filtered, and evaporated. The title compound was obtained as a white solid by silica gel chromatography (50 mg, 65%). $^1$H NMR (400 MHz, $CDCl_3$) δ 9.65 (br s, 1H), 7.48 (d, J=4 Hz, 1H), 7.21 (d, J=8 Hz, 2H), 7.01 (d, J=4 Hz, 1H), 6.78 (d, J=8 Hz, 2H), 5.18 (s, 1H), 4.65 (d, J=15 Hz, 1H), 4.31 (d, J=15 Hz, 1H), 3.76 (d, J=14 Hz, 1H), 3.68 (m, 4H), 1.87 (overlapping singlets, 6H). MS: m/z ($MNa^+$) 410.

Example 32

2-[1-(4-Methoxy-benzyl)-3,4-dimethyl-5-oxo-2,5-dihydro-1H-pyrrol-2-ylsulfanyl]-N-pyridin-2-yl-propionamide (Compound 32)

A. 2-[1-(4-Methoxy-benzyl)-3,4-dimethyl-5-oxo-2,5-dihydro-1H-pyrrol-2-ylsulfanyl]-propionic acid The compound prepared in Part B of Example 1 (0.36 g, 1.45 mmol), thiolactic acid (0.128 mL, 1.45 mmol) and a catalytic amount of p-toluene sulfonic acid in dichloromethane (3 mL) were stirred at room temperature for 6 hr. Water (15 mL) and $CH_2Cl_2$ (15 mL) were added and layers were separated. The organic layer was washed with brine (1×), dried over $MgSO_4$, and evaporated in vacuo. Further purification by acid/base extraction provide the title compound. (0.230 g, 47%).

B. 2-[1-(4-Methoxy-benzyl)-3,4-dimethyl-5-oxo-2,5-dihydro-1H-pyrrol-2-ylsulfanyl]-N-pyridin-2-yl-propionamide The product from Part A (0.17 g, 0.50 mmol) was treated as described in Part B of Example 16 to provide two diastereomers of the title compound (25.6 g, and 23.9 g). $^1$H NMR (400 MHz, $CDCl_3$) δ8.64 (broad s, 1H); 8.25 (m, 1H); 8.18 (d, J=8.4 Hz, 1H); 7.73 (t, J=8.5 Hz, 1H); 7.21 (d, J=8.6 Hz, 2H); 7.09 (m, 1H); 6.82 (d, J=8.6 Hz, 2H); 5.18 (d, 15 Hz, 1H); 4.61 (s, 1H); 4.19 (d, J=15 Hz, 1H); 3.77 (s, 3H); 2.92 (q, J=7.33 Hz, 1H); 1.89 (s, 3H); 1.80 (s, 3H); 1.5 (d, J=7.36, 3H). MS: m/z ($MH^+$) 412. $^1$H NMR (400 MHz, $CDCl_3$) δ 8.50 (broad s, 1H); 8.28 (m, 1H); 8.15 (d, J=8.4 Hz, 1H); 7.75 (t, J=8.5 Hz, 1H); 7.15 (d, J=8.6 Hz, 2H); 7.09 (m, 1H); 6.80 (d, J=8.6 Hz, 2H); 4.98 (d, 15 Hz, 1H); 4.61 (s, 1H); 4.10 (d, J=15

Hz, 1H); 3.77 (s, 3H); 3.0 (q, J=7.33 Hz, 1H); 1.99 (s, 3H); 1.89 (s, 3H); 1.5 (d, J=7.36, 3H). MS: m/z (MH⁺) 412.

Example 33

6-{(2-[1-(4-Methoxy-benzyl)-3,4-dimethyl-5-oxo-2,5-dihydro-1H-pyrrol-2-ylsulfanyl]-acetylamino}-nicotinic acid (Compound 33)

A. (6-Amino-pyridin-3-yl)-trimethylsilanyl-methanone

6-Aminonicotinic acid (86 mg, 0.6 mmol) was taken up in 0.65 mL pyridine and 10 mL $CH_2Cl_2$. Chlorotrimethylsilane (0.65 mL, 7 mmol) was added and the mixture stirred for 6 h. Solvent was evaporated and the product was used without purification.

B. 6-{2-[1-(4-Methoxy-benzyl)-3,4-dimethyl-5-oxo-2,5-dihydro-1H-pyrrol-2-ylsulfanyl]-acetylamino}-nicotinic acid The total product from Part A and the product from Example 1, Part C (100 mg, 0.3 mmol) were converted to the title compound by the method described in Example 5, with an additional EtOAc/water wash after chromatography to remove the silyl ester protecting group (105 mg, 77%). ¹H NMR (400 MHz, DMSO) δ 13.14 (br s, 1H), 10.95 (s, 1H), 8.81 (s, 1H), 8.26 (d, J=9 Hz, 1H), 8.11 (d, J=9 Hz, 1H), 7.12 (d, J=8 Hz, 2H), 6.85 (d, J=8 Hz, 2H), 4.87 (s, 1H), 4.79 (d, J=15 Hz, 1H), 4.14 (d, J=15 Hz, 1H), 3.70 (s, 3H), 3.12 (d, J=15 Hz, 1H), 3.07 (d, J=15 Hz, 1H), 1.90 (s, 3H), 1.68 (s, 3H). MS: m/z (MH⁺) 442.

Example 34

2-[1-(4-Dimethylamino-benzyl)-3,4-dimethyl-5-oxo-2,5-dihydro-1H-pyrrol-2-ylsulfanyl]-N-pyridin-2-yl-acetamide (Compound 34)

A. [1-(4-Dimethylamino-benzyl)-3,4-dimethyl-5-oxo-2,5-dihydro-1H-pyrrol-2-ylsulfanyl]-acetic acid The title compound was prepared by the method described in Parts A, B and C of Example 1 substituting the 4-methoxybenzylamine with 4-dimethylaminobenzylamine in Part A.

B. 2-[1-(4-Dimethylamino-benzyl)-3,4-dimethyl-5-oxo-2,5-dihydro-1H-pyrrol-2-ylsulfanyl]-N-pyridin-2-yl-acetamide The product of Part A (0.078 g, 0.23 mmol) was treated by the method described in Part B of Example 16 to provide the title compound (37.8 mg, 39%). ¹H NMR (400 MHz, CDCl₃) δ 8.55 (broad s, 1H); 8.27 (m, 1H); 8.14 (d, J=7.6 Hz, 1H); 7.71 (t, J=7 Hz, 1H); 7.18 (d, J=8.3 Hz, 2H); 7.06 (m, 1H); 6.66 (t, J=8.4 Hz, 2H); 5.08 (d, J=14.5 Hz, 1H); 4.63 (s, 1H); 4.11 (d, 14.5 Hz, 1H); 2.91 (s, 8H); 1.93 (s, 3H); 1.83 (s, 3H). MS: m/z (MH⁺) 411.

Example 35

6-{2-[1-(4-Fluoro-benzyl)-3,4-dimethyl-5-oxo-2,5-dihydro-1H-pyrrol-2-ylsulfanyl]-acetylamino}-nicotinic acid methyl ester (Compound 35)

The compound prepared in Part A of Example 12 (0.29 g, 0.94 mmol) and 6-aminonicotinic acid methyl ester (0.214 g, 1.40 mmol) was converted to the title compound (0.232 g, 56%) following the procedure described in Part B of Example 16. ¹H NMR (400 MHz, CDCl₃) δ 8.86 (s, 2H); 8.32 (d, J=8.7 Hz, 1H), 8.22 (d, J=8.7 Hz, 1H); 7.28 (m, 2H); 7.01 (m, 2H); 5.16 (d, J=15 Hz, 1H), 4.62 (s, 1H); 4.21 (d, 15 Hz, 1H); 3.93 (s, 3H); 3.04 (d, J=16 Hz, 1H), 2.96 (d, J=16 Hz, 1H), 1.95 (s, 3H); 1.84 (s, 3H). MS: m/z (MH⁺) 444.

Example 36

6-{2-[1-(4-Difluoromethoxy-benzyl)-3,4-dimethyl-5-oxo-2,5-dihydro-1H-pyrrol-2-ylsulfanyl]-acetylamino}-nicotinic acid methyl ester (Compound 36)

The compound prepared in Part A of Example 16 (0.15 g, 0.43 mmol) and 6-aminonicotinic acid methyl ester (97 mg, 0.63 mmol) was converted to the title compound (0.073 g, 35%) following the procedure described in Part B of Example 16. ¹H NMR (400 MHz, CDCl₃) δ 8.97 (s, 1H); 8.83 (s, 1H); 8.32 (d, J=8.7 Hz, 1H), 8.22 (d, J=8.7 Hz, 1H); 7.28 (d, J=8.6 Hz, 2H); 7.06 (d, J=8.6 Hz, 2H); 6.5 (s, 1H); 5.19 (d, J=15 Hz, 1H), 4.63 (s, 1H); 4.23 (d, 15 Hz, 1H); 3.93 (s, 3H); 3.04 (d, J=16 Hz, 1H), 2.96 (d, J=16 Hz, 1H), 1.95 (s, 3H); 1.84 (s, 3H). MS: m/z (MH⁺) 492.

Example 37

6-{(2-[1-(2,3-Dihydro-benzofuran-5-ylmethyl)-3,4-dimethyl-5-oxo-2,5-dihydro-1H-pyrrol-2-ylsulfanyl]-acetylamino}-nicotinic acid methyl ester (Compound 37)

The compound prepared in Part A of Example 20 (0.30 g, 0.91 mmol) and 6-aminonicotinic acid methyl ester (0.21 g, 1.36 mmol) was converted to the title compound (0.210 g, 49%) following the procedure described in Part B of Example 16. ¹H NMR (400 MHz, CDCl₃) δ 9.07 (s, 1H); 8.85 (s, 1H); 8.31–8.22 (m, 2H), 7.14 (s, 1H); 7.03 (d, J=8 Hz, 1H); 6.07 (d, J=8 Hz, 1H); 5.14 (d, J=14.4 Hz, 1H), 4.64 (s, 1H); 4.56 (t, J=8.9 Hz, 2H); 4.14 (d, 14.4 Hz, 1H); 3.87 (s, 3H); 3.17 (t, J=8.5 Hz, 2H); 3.08 (d, J=16 Hz, 1H), 3.02 (d, J=16 Hz, 1H), 1.95 (s, 3H); 1.84 (s, 3H). MS: m/z (MH⁺) 468.

Example 38

6-[2-(3,4-Dimethyl-5-oxo-1-thiophen-2-ylmethyl-2,5-dihydro-1H-pyrrol-2-ylsulfanyl)-acetylamino]-nicotinic acid methyl ester (Compound 38)

The compound prepared in Part A of Example 24 (0.31 g, 1.05 mmol) and 6-aminonicotinic acid methyl ester (0.24 g, 1.57 mmol) was converted to the title compound (0.270 g, 60%) following the procedure described in Part B of Example 16. ¹H NMR (400 MHz, CDCl₃) δ 8.14 (s, 1H); 8.85 (s, 1H); 8.30 (d, J=8.7 Hz, 1H), 8.24 (d, J=8.7 Hz, 1H); 7.21 (d, J=5, 1H); 7.02 (s, 1H); 6.94 (m, 1H); 5.32 (d, J=15 Hz, 1H), 4.77 (s, 1H); 4.51 (d, 15 Hz, 1H); 3.92 (s, 3H); 3.12 (d, J=16 Hz, 1H), 3.03 (d, J=16 Hz, 1H), 1.95 (s, 3H); 1.84 (s, 3H). MS: m/z (MH⁺) 432.

Example 39

6-{(2-[1-(3,4-Dimethoxy-benzyl)-3,4-dimethyl-5-oxo-2,5-dihydro-1H-pyrrol-2-ylsulfanyl]-acetylamino}-nicotinic acid methyl ester (Compound 39)

The compound prepared in Part A of Example 11 (0.26 g, 0.74 mmol) and 6-aminonicotinic acid methyl ester (0.17 g, 1.13 mmol) was converted to the title compound (0.110 g, 30%) following the procedure described in Part B of Example 16. $^1$H NMR (400 MHz, CDCl$_3$) δ 8.97 (s, 1H); 8.85 (s, 1H); 8.31 (d, J=8.7 Hz, 1H), 8.24 (d, J=8.7 Hz, 1H); 6.85–6.77 (m, 3H); 5.16 (d, J=15 Hz, 1H), 4.63 (s, 1H); 4.14 (d, 15 Hz, 1H); 3.92 (s, 3H); 3.84 (s, 3H); 3.83 (s, 3H); 3.02 (d, J=16 Hz, 1H), 3.00 (d, J=16 Hz, 1H), 1.95 (s, 3H); 1.84 (s, 3H). MS: m/z (MH$^+$) 486.

Example 40

6-{(2-[1-(3,5-Dimethoxy-benzyl)-3,4-dimethyl-5-oxo-2,5-dihydro-1H-pyrrol-2-ylsulfanyl]-acetylamino}-nicotinic acid methyl ester (Compound 40)

The compound prepared in Part A of Example 29 (0.31 g, 0.88 mmol) and 6-aminonicotinic acid methyl ester (0.20 g, 1.32 mmol) was converted to the title compound (0.21 g, 49%) following the procedure described in Part B of Example 16. $^1$H NMR (400 MHz, CDCl$_3$) δ 9.12 (s, 1H); 8.85 (s, 1H); 8.32 (d, J=8.7 Hz, 1H), 8.23 (d, J=8.7 Hz, 1H); 6.42 (s, 2H); 6.34 (s, 1H); 5.18 (d, J=15 Hz, 1H), 4.67 (s, 1H); 4.14 (d, 15 Hz, 1H); 3.92 (s, 3H); 3.75 (s, 6H); 3.09 (d, J=16 Hz, 1H), 3.03 (d, J=16 Hz, 1H), 1.95 (s, 3H); 1.83 (s, 3H). MS: m/z (MH$^+$) 486.

D) General Administration, Formulation, and Dosages

The present compounds are glucokinase modulators and are therefore useful in treating, preventing, or inhibiting the progression of glucokinase mediated conditions, such as metabolic disorders including diabetes, diabetes, obesity, and associated symptoms or complications thereof. In particular, a glucokinase mediated condition can be selected, for example, from diabetes such as IDDM and NIDDM, obesity, IGT (Impaired Glucose Tolerance), IFG (Impaired Fasting Glucose), Syndrome X (or Metabolic Syndrome), and insulin resistance.

The invention features a method for treating a subject with a glucokinase mediated disease, said method comprising administering to the subject a therapeutically effective amount of a pharmaceutical composition comprising a compound of the invention. The invention also provides a method for treating or inhibiting the progression of diabetes, obesity, and associated symptoms or complications thereof in a subject, wherein the method comprises administering to the subject a therapeutically effective amount of a pharmaceutical composition comprising a compound of the invention.

Pharmaceutically acceptable salts include the therapeutically active non-toxic salts of disclosed compounds. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term "salt" also comprises the solvates which the disclosed compounds, as well as the salts thereof, are able to form. Such solvates are for example hydrates, alcoholates and the like. Conversely the salt form can be converted by treatment with alkali into the free base form.

Stereoisomeric forms define all the possible isomeric forms which the compounds of the invention may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

The next section includes detailed information relating to the use of the disclosed compounds and compositions.

E) Use

The compounds of the present invention are pharmaceutically active, for example, as glucokinase modulators. Examples of glucokinase-mediated diseases include diabetes such as IDDM and NIDDM, obesity, IGT (Impaired Glucose Tolerance), IFG (Impaired Fasting Glucose), Syndrome X (or Metabolic Syndrome), hyperglycemia, elevated blood glucose level, and insulin resistance.

According to one aspect of the invention, the disclosed compounds and compositions are useful for the amelioration of symptoms associated with, the treatment of, and the prevention of, the following conditions and diseases: diabetes such as IDDM and NIDDM, obesity, IGT (Impaired Glucose Tolerance), IFG (Impaired Fasting Glucose), Syndrome X (or Metabolic Syndrome), hyperglycemia, elevated blood glucose level, and insulin resistance.

According to one aspect of the invention, the disclosed compounds may be used in a method for treating or inhibiting the progression of a glucokinase-mediated condition and, optionally, an additional glucokinase mediated condition, said method comprising administering to a patient in need of treatment a pharmaceutically effective amount of a composition of the invention.

Another aspect of the invention is a method of use wherein the glucokinase-mediated condition is IDDM, d NIDDM, obesity, IGT (Impaired Glucose Tolerance), IFG (Impaired Fasting Glucose), Syndrome X (or Metabolic Syndrome), hyperglycemia, elevated blood glucose level, and insulin resistance.

The invention also features pharmaceutical compositions which include, without limitation, one or more of the disclosed compounds, and pharmaceutically acceptable carriers or excipients.

1. Dosages

Those of skill in the treatment of disorders or conditions mediated by glucokinase could easily determine the effective daily amount from the test results presented hereinafter and other information. The exact dosage and frequency of administration depends on the particular compound of invention used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg/kg to about 300 mg/kg (preferably from about 0.01 mg/kg to about 100 mg/kg; and, more preferably, from about 0.01 mg/kg to about 30 mg/kg) and may be given at a dosage of from about 0.01 mg/kg/day to about 300 mg/kg/day (preferably from about 0.01 mg/kg/day to about 100 mg/kg/day, more preferably from about 0.01 mg/kg/day to about 30 mg/kg/day and even more preferably from about 0.01 mg/kg/day to about 10 mg/kg/day). Preferably, the method for the treatment of metabolic disorders described in the present invention using any of the compounds as defined herein, the dosage form will contain a pharmaceutically acceptable carrier containing between from about 0.01 mg to about 100 mg; and, more preferably, from about 5 mg to about 50 mg of the compound, and may be constituted into any form suitable for the mode of administration selected. The dosages, however, may be varied depending upon the requirement of the subjects, the severity of the condition being treated and the compound being employed. The use of either daily administration or post-periodic dosing may be employed.

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of this invention may be administered in any of the foregoing compositions and dosage regimens or by means of those compositions and dosage regimens established in the art whenever treatment of glucokinase mediated disorders is required for a subject in need thereof.

The daily dose of a pharmaceutical composition of the present invention may be varied over a wide range from about 0.7 mg to about 500 mg per adult human per day; preferably, the dose will be in the range of from about 0.7 mg to about 100 mg per adult human per day; most preferably the dose will be in the range of from about 0.7 mg to about 50 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. An effective amount of the drug is ordinarily supplied at a dosage level of from about 0.01 mg/kg to about 300 mg/kg of body weight per day. Advantageously, a compound of the present invention may be administered in a single daily dose or the total daily dosage may be administered in divided doses of two, three or four times daily.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

2. Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

3. Combination Therapy

The compounds of the present invention may be used in combination with one or more pharmaceutically active agents. These agents include other glucokinase modulators, anti-diabetic agents, other lipid lowering agents, direct thrombin inhibitor (DTI), as well as blood pressure lowering agents such as statin drugs and the fibrates.

Other glucokinase modulators include:

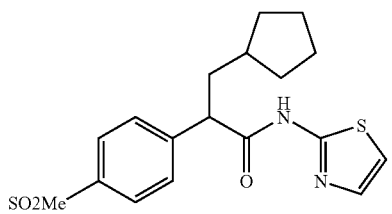

Ro-28-1675

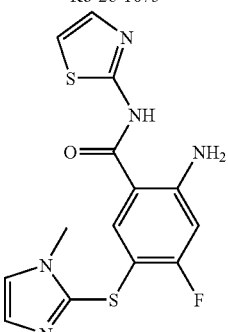

Banyu/Merck glucokinase acitvator

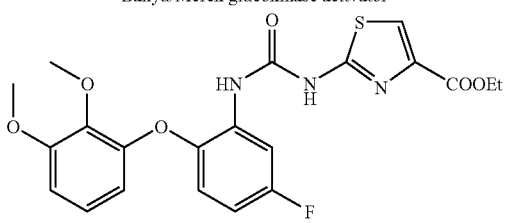

Novo Nordisk IV

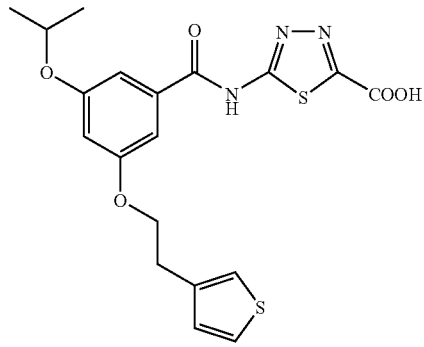

Astra Zeneca glucokinase activator

Anti-diabetic agents include RXR modulators such as:
(1) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455);
(2) 9-cis-retinoic acid;
(3) AGN-4326 (also known as ALRT-4204, AGN-4204, ALRT-326, ALRT-324, or LGD 1324);
(4) LGD 1324 (ALRT 324);
(5) LG 100754;
(6) LY-510929;
(7) LGD 1268 (6-(1,1,4,4,6-pentamethyl-1,2,3,4-tetrahydro-naphth-7-ylcycloprop-1-yl) nicotinic acid, known as ALRT 268 or LG 100268);
(8) LG 100264; and (9) substituted heterocycles as disclosed in PCT publications WO 01/16122 and WO 01/16123 by Maxia.

One preferred example of substituted heterocycles is MX-6054, which is 2,4-thiazolidinedione, 5-[[3-(5,6,7,8-tetrahydro-3,5,5,8,8-pentamethyl-2-naphthalenyl)-4-(trifluoromethoxy)phenyl]methylene]-, (5Z)-, also named 3-(3,5,5,8,8-pentamethyl-5,6,7,8-tetrahydro-2-naphthyl)-4-trifluoromethoxybenzylidene-2,4-thiazolidinedione, represented by the following formula:

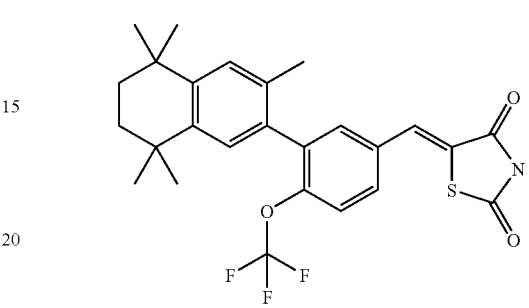

Another preferred example of substituted heterocycles is 2,4-thiazolidinedione, 5-[[3-(1-ethyl-1,2,3,4-tetrahydro-4,4,6-trimethyl-2-oxo-7-quinolinyl)-4-(trifluoromethoxy)phenyl]methylene]-, (5Z)-, represented by the following formula:

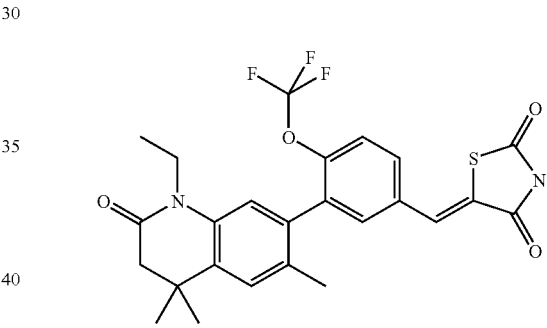

Preferred substituted heterocycles are selected from:
3-(3,5,5,8,8-pentamethyl-5,6,7,8-tetrahydro-2-naphthyl)-4-trifluoromethoxybenzylidene-2,4-thiazolidinedione;
4-[2-(3,5,5,8,8-pentamethyl-5,6,7,8-tetrahydro-2-naphthyl)-1,3-dioxolane]benzylidene-2,4-thiazolidinedione;
4-[2-(5,5,8,8-tetramethyl-5,6,7,8-tetrahydro-2-naphthyl)-2-propyl]benzylidene-2,4-thiazolidinedione;
4-[2-(3,5,5,8,8-pentamethyl-5,6,7,8-tetrahydro-2-naphthyl)-1,3-dioxolane]benzylidene-2-thioxo-2,4-thiazolidinedione;
4-[2-(5,5,8,8-tetramethyl-5,6,7,8-tetrahydro-2-naphthyl)-2-propyl]benzylidene-2-thioxo-2,4-thiazolidinedione;
4-[2-(3,5,5,8,8-pentamethyl-5,6,7,8-tetrahydro-2-naphthyl)-1,3-dioxolane]benzylidene-2-thioxo-2,4-imidazolidinedione;
4-[2-(5,5,8,8-tetramethyl-5,6,7,8-tetrahydro-2-naphthyl)-2-propyl]benzylidene-2-thioxo-2,4-imidazolidinedione;
4-[2-(3,5,5,8,8-pentamethyl-5,6,7,8-tetrahydro-2-naphthyl)-1,3-dioxolane]benzylidene-2,4-imidazolidinedione;
4-[2-(5,5,8,8-tetramethyl-5,6,7,8-tetrahydro-2-naphthyl)-2-propyl]benzylidene-2,4-imidazolidinedione;
4-[2-(3,5,5,8,8-pentamethyl-5,6,7,8-tetrahydro-2-naphthyl)-1,3-dioxolane]benzyl-2,4-thiazolidinedione;

4-[2-(5,5,8,8-tetramethyl-5,6,7,8-tetrahydro-2-naphthyl)-2-propyl]benzyl-2,4-thiazolidinedione;
4-[2-(3,5,5,8,8-pentamethyl-5,6,7,8-tetrahydro-2-naphthyl)-1,3-dioxolane]benzyl-2-thioxo-2,4-thiazolidinedione;
4-[2-(5,5,8,8-tetramethyl-5,6,7,8-tetrahydro-2-naphthyl)-2-propyl]benzyl-2-thioxo-2,4-thiazolidinedione;
4-[2-(3,5,5,8,8-pentamethyl-5,6,7,8-tetrahydro-2-naphthyl)-1,3-dioxolane]benzyl-2-thioxo-2,4-imidazolidinedione;
4-[2-(5,5,8,8-tetramethyl-5,6,7,8-tetrahydro-2-naphthyl)-2-propyl]benzyl-2-thioxo-2,4-imidazolidinedione;
4-[2-(3,5,5,8,8-pentamethyl-5,6,7,8-tetrahydro-2-naphthyl)-1,3-dioxolane]benzyl-2,4-imidazolidinedione; and
4-[2-(5,5,8,8-tetramethyl-5,6,7,8-tetrahydro-2-naphthyl)-2-propyl]benzyl-2,4-imidazolidinedione.

Anti-diabetic agents also include thiazolidinedione and non-thiazolidinedione insulin sensitizers, which decrease peripheral insulin resistance by enhancing the effects of insulin at target organs and tissues.

The following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:

(1) rosiglitazone (2,4-thiazolidinedione,5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);

(2) pioglitazone (2,4-thiazolidinedione, 5-((4-(2-(5-ethyl-2-pyridinyl) ethoxy)phenyl)methyl)-, monohydrochloride, (+−)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));

(3) troglitazone (5-((4-((3,4-dihydro-6-hydroxy-2,5,7,8-tetramethyl-2H-1-benzopyran-2-yl) methoxy)phenyl) methyl)-2,4-thiazolidinedione, known as NOSCAL, REZULIN, ROMOZIN, or PRELAY; also known as Cl991, CS 045, GR 92132, GR 92132×);

(4) isaglitazone ((+)-5-[[6-[(2-fluorophenyl)methoxy]-2-naphthalenyl]methyl]-2,4-thiazolidinedione or 5-((6-((2-fluorophenyl) methoxy)-2-naphthalenyl) methyl-2,4-thiazolidinedione or 5-(6-(2-fluorobenzyloxy) naphthalen-2-ylmethyl) thiazolidine-2,4-dione, also known as MCC-555 or neoglitazone); and (5) 5-BTZD.

Additionally, the non-thiazolidinediones that act as insulin sensitizing agents include, but are not limited to:

(1) JT-501 (JTT 501, PNU-1827, PNU-716-MET-0096, or PNU 182716: isoxazolidine-3,5-dione, 4-((4-(2-phenyl-5-methyl)-1,3-oxazolyl)ethylphenyl-4) methyl-);

(2) KRP-297 (5-(2,4-dioxothiazolidin-5-ylmethyl)-2-methoxy-N-(4-(trifluoromethyl) benzyl) benzamide or 5-((2,4-dioxo-5-thiazolidinyl) methyl)-2-methoxy-N-((4-(trifluoromethyl)phenyl)methyl) benzamide); and (3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl) ethyl)-L-tyrosine, or GW2570 or GI-262570).

Other anti-diabetic agents have also been shown to have PPAR modulator activity such as PPAR gamma, SPPAR gamma, and/or PPAR delta/gamma agonist activity. Examples are listed below:

(1) AD 5075;
(2) R 119702 ((+−)-5-(4-(5-Methoxy-1H-benzimidazol-2-ylmethoxy) benzyl)thiazolin-2,4-dione hydrochloride, or Cl1037 or CS 011);
(3) CLX-0940 (peroxisome proliferator-activated receptor alpha agonist/peroxisome proliferator-activated receptor gamma agonist);
(4) LR-90 (2,5,5-tris(4-chlorophenyl)-1,3-dioxane-2-carboxylic acid, PPAR delta/γ agonist);
(5) Tularik (PPAR γ agonist);
(6) CLX-0921 (PPAR γ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl) amino)-2-oxoethyl)-2-heptyl-4-oxo-3-thiazo lidinyl) butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-O-(2-(methyl-2-pyridinylamino) ethyl)-L-tyrosine, known as GW 2331, PPAR alpha/γ agonist);
(23) SB 219994 ((S)-4-(2-(2-benzoxazolylmethylamino) ethoxy)-alpha-(2,2,2-trifluoroethoxy)benzen epropanoic acid or 3-(4-(2-(N-(2-benzoxazolyl)-N-methylamino)ethoxy)phenyl)-2 (S)-(2,2,2-trifluoroethoxy) propionic acid or benzenepropanoic acid, 4-(2-(2-benzoxazolylmethylamino)ethoxy)-alpha-(2,2,2-trifluoroethoxy)-(alphaS)-, PPAR alpha/γ agonist);
(24) L-796449 (PPAR alpha/γ agonist);
(25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPA R alpha agonist);
(26) GW-9578 (PPAR alpha agonist);
(27) GW-2433 (PPAR alpha/γ agonist);
(28) GW-0207 (PPAR γ agonist);
(29) LG-100641 (PPAR γ agonist);
(30) LY-300512 (PPAR γ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR alpha/γ agonist).

Other insulin sensitizing agents include, but are not limited to:

(1) INS-1 (D-chiro inositol or D-1,2,3,4,5,6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)—N-(2-(4-(carboxymethyl)phenoxy)ethyl)-N-(2-hydroxy-2-phenethyl) ammonium chloride, also known as ICI D 2079) or AZ 40140;
(5) glycogen phosphorylase inhibitors;

(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis(1,4-phenylene) bismethylenebis (thiazolidine-2,4-dione);
(12) TS 971;
(13) T 174 ((+−)-5-(2,4-dioxothiazolidin-5-ylmethyl)-2-(2-naphthylmethyl)benzoxazole);
(14) SDZ PGU 693 ((+)-trans-2 (S-((4-chlorophenoxy) methyl)-7alpha-(3,4-dichlorophenyl)tetrahydropyrrolo (2,1-b) oxazol-5(6H)-one);
(15) S 15261 ((−)-4-(2-((9H-fluoren-9-ylacetyl)amino) ethyl)benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl)hydrazino) acetic acid;
(20) PNU 106817 (2-(hydrazinoiminomethyl)hydrazino) acetic acid;
(21) NC 2100 (5-((7-(phenylmethoxy)-3-quinolinyl)methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl) ethoxy) benzyl)-malonic acid dimethyl diester);
(27) Dexlipotam (5 (R)-(1,2-dithiolan-3-yl)pentanoic acid, also known as (R)-alpha lipoic acid or (R)-thioctic acid);
(28) BM 170744 (2,2-Dichloro-12-(p-chlorophenyl)dodecanoic acid);
(29) BM 152054 (5-(4-(2-(5-methyl-2-(2-thienyl)oxazol-4-yl) ethoxy)benzothien-7-ylmethyl)thiazolidine-2,4-dione);
(30) BM 131258 (5-(4-(2-(5-methyl-2-phenyloxazol-4-yl) ethoxy) benzothien-7-ylmethyl)thiazolidine-2,4-dione);
(31) CRE 16336 (EML 16336);
(32) HQL 975 (3-(4-(2-(5-methyl-2-phenyloxazol-4-yl) ethoxy) phenyl)-2 (S)-(propylamino)propionic acid);
(33) DRF 2189 (5-((4-(2-(1-Indolyl)ethoxy)phenyl)methyl)thiazolidine-2,4-dione);
(34) DRF 554158;
(35) DRF—NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

Anti-diabetic agents can further include biguanides, which decreases liver glucose production and increases the uptake of glucose. Examples of biguanides include metformin such as:

(1) 1,1-dimethylbiguanide (e.g., Metformin-DepoMed, Metformin-Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

Additionally, anti-diabetic agents include alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the postprandial glucose peak. Examples of alpha-glucosidase inhibitors include, but are not limited to:

(1) acarbose (D-glucose, O-4,6-dideoxy-4-(((1S-(1alpha, 4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl) (2R (2alpha, 3beta, 4alpha, 5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);
(4) emiglitate(4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542);
(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose(3,4-dideoxy-4-((2-hydroxy-1-(hydroxymethyl)ethyl) amino)-2-C-(hydroxymethyl)-D-epi-inositol or D-epi-Inositol, 3,4-dideoxy-4-((2-hydroxy-1-(hydroxymethyl)ethyl)amino)-2-C-(hydroxymethyl)-, also known as A 71100, AO 128, BASEN, GLUSTAT, VOGLISTAT.

Anti-diabetic agents also include insulins such as regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:

(1) Biota;
(2) LP 100;
(3) (SP-5-21)-oxobis(1-pyrrolidinecarbodithioato-S,S') vanadium;
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N-6-(1-oxotetradecyl)-L-lysine)-(1A-21A), (1B-29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.

Anti-diabetic agents can also include insulin secretion modulators such as:

(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
    (4a) DPP-728 or LAF 237 (2-pyrrolidinecarbonitrile,1-(((2-((5-cyano-2-pyridinyl)amino)ethyl)amino) acetyl), known as NVP-DPP-728, DPP-728A, LAF-237);
    (4b) P 3298 or P32/98 (di-(3N-((2S,3S)-2-amino-3-methyl-pentanoyl)-1,3-thiazolidine) fumarate);
    (4c) TSL 225 (tryptophyl-1,2,3,4-tetrahydroisoquinoline-3-carboxylic acid);
    (4d) Valine pyrrolidide (valpyr);
    (4e) 1-aminoalkylisoquinolinone-4-carboxylates and analogues thereof;
    (4f) SDZ 272-070 (1-(L-Valyl)pyrrolidine);
    (4g) TMC-2A, TMC-2B, or TMC-2C;
    (4h) Dipeptide nitriles (2-cyanopyrrolodides);
    (4i) CD26 inhibitors; and
    (4j) SDZ 274-444;
(5) glucagon antagonists such as AY-279955; and
(6) amylin agonists which include, but are not limited to, pramLintide (AC-137, SymLin, tripro-amylin or pramLintide acetate).

Well-known anti-diabetic agents include insulin, sulfonylureas, biguanides, meglitinides, AGI's (Alpha-Glucosidase Inhibitors; e.g., Glyset), PPAR alpha agonists, and PPAR gamma agonists, and dual PPAR alpha/gamma agonists.

Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include antihypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

In addition, a second glucokinase modulator, as described above in Section B), may also be utilized as a third antidiabetic agent, provided that it is different from the first glucokinase modulator.

F) Biological Example

Glucokinase Enzyme Assay

An enzymatic Glucokinase (GK) assay using purified recombinant human liver/pancreas enzyme was used to evaluate the effects of potential small molecule modulators.

In this assay, GK catalyzes glucose phosphorylation in the presence of ATP. The product of this reaction, glucose-6-phosphate, was then oxidized by an excess of glucose-6-phosphate dehydrogenase to produce gluconate-6-phosphate with concomitant reduction of nicotinamide adenine dinucleotide (NAD). Production of reduced adenine dinucleotide (NADH) resulted in increase in fluorescence, which was used to monitor GK activity. Human GK (Liver/Pancreas) was expressed in *Escherichia coli* as a (His) 6-tagged fusion protein and was purified by metal chelate affinity chromatography. The assay was performed in a final incubation volume of 80 µl in a 96-well clear low UV absorption plates. The incubation mixture consisted of 25 mM HEPES, 2 mM MgSO$_4$, 1 mM dithiothreotol (DTT), 1 mg/mL bovine serum albumin (BSA), 1 mM ATP, 1 mM NAD, and 12 mM glucose, 10 units per mL glucose-6-phosphate dehydrogenase, and +/−300 ng per mL GK. For determination of the affinity ($K_m$) and $V_{max}$, different concentrations of glucose ranging from 0.5 mM to 40 mM were used in the assay; see Grimsby, J., Sarabu, R.; Grippo, J. F.; et. al. Science 2003, 301, 370-373. Production of reduced NAD (Nicotinamide Adenine Dinucleotide) was measured as changes in absorption at 340 nm in 96-well plate reader (Envision model #2101 Multilabel Plate reader). % Activation @ 50 µM was calculated as the percentage increase in GK activity above the vehicle control with the effective concentration of the compound being 50 µM. $EC_{50\%}$ (µM) was calculated as the effective concentration of the compound that produces 50% activation above the vehicle control, and $EC_{100\%}$ (µM) was calculated as the effective concentration of the compound that produces 100% activation above the vehicle control.

Compounds listed in Tables II and III below were tested in the above assay(s):

TABLE II

Liver GK data

| Compound # | % Activation @ 50 μM | $EC_{50\%}$ (μM) | $EC_{100\%}$ (μM) |
|---|---|---|---|
| 1 | 291 236 | 0.39 0.26 | 1.46 |
| 2 | 169 | 9.4 | — |
| 3 | 64.9 | — | — |
| 4 | 199 139 | 24.5 19.8 | 30.4 37.3 |
| 5 | 222 | 3.3 | 8.3 |
| 6 | 175 | 6.3 | 20.1 |
| 7 | 114 | 11.6 | 38.9 |
| 8 | 169 | 2.72 | 9.77 |
| 9 | 215 | 1.4 | 4.9 |
| 10 | 128 | 12.2 | 39.92 |
| 11 | 243 | 2.41 | 5.83 |
| 12 | 198 | 2.9 | 8.72 |
| 14 | 19 9 | — | — |
| 15 | 122 121 105 | 10.05 | 37.08 |
| 16 | 166 160 150 | 6.76 | 17.01 |
| 17 | 68 44 | — | — |
| 18 | 217 209 | 1.13 | 3.61 |
| 19 | 153 99 | 13.8 | 30.5 |
| 20 | 255 183 | 2.78 | 6.61 |
| 21 | 133 175 | 4.73 | 12.68 |
| 22 | 82 94 | 17.28 | — |
| 23 | 161 205 | 6.23 | 13.78 |
| 24 | 172 | 8.4 | 26.7 |
| 25 | 180 | 6.3 | 28.5 |
| 26 | 154 | 15.3 | 35.9 |
| 27 | 90 87 | 14.1 | >50 |
| 28 | 90 92 | 14.2 | >50 |
| 29 | 185 133 | 7.7 | 26.1 |
| 30 | 80 59 | 34.5 | >50 |
| 31 | 21 | — | — |
| 32 | 37 | — | — |

TABLE III

Pancreas GK data

| Compound # | % Activation @ 50 μM | $EC_{50\%}$ (μM) | $EC_{100\%}$ (μM) |
|---|---|---|---|
| 1 | 287 | 0.64 | 2.23 |
| 18 | 167 156 | 3.51 | 12.02 |
| 19 | 113 82 | 15.2 | 47.3 |
| 20 | 198 145 | 3.23 | 8.87 |
| 21 | 113 140 | 7.12 | 19.43 |
| 22 | 70 72 | 24.1 | — |
| 23 | 130 161 | 8.13 | 20.28 |
| 24 | 124 | 13.6 | 37.3 |
| 25 | 130 | 14.7 | 44.9 |
| 26 | 102 | 24 | — |
| 27 | 55 77 | 20 | >50 |
| 28 | 57 83 | 18.5 | >50 |
| 29 | 147 110 | 11.8 | 41.4 |
| 30 | 48 20 | >50 | >50 |
| 31 | 3 | — | — |
| 32 | 24 | — | — |
| 33 | 181 190 341 | 2.5 1.6 | 19 6.5 |
| 34 | 163.2 172.3 | 2.5 | 12 |
| 35 | 155.7 174.8 | 0.98 | 5.3 |
| 36 | 158.6 127.1 | 2.5 | 18 |
| 37 | 208.6 200 | 1.09 | 1.09 |

TABLE III-continued

Pancreas GK data

| Compound # | % Activation @ 50 μM | $EC_{50\%}$ (μM) | $EC_{100\%}$ (μM) |
|---|---|---|---|
| 38 | 190.9 140.4 | 1.09 | 8.9 |
| 39 | 204.1 180.4 | 1.139 | 5.3 |
| 40 | 159.9 139.7 | 2.3 | 19 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:
1. A compound of Formula (I)

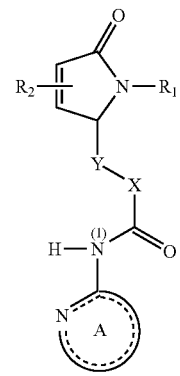

wherein
X is $C_{1-4}$alkylene, wherein the $C_{1-4}$alkylene is optionally substituted with one to three groups selected from $C_{1-3}$alkyl and halo;
wherein said $C_{1-3}$alkyl is optionally substituted with one to three groups selected from oxo, amino, alkoxy, carboxy, nitro, hydroxyl, and halo;
Y is S or S(O);
$R_1$ is H or $C_{1-6}$alkyl, wherein the $C_{1-6}$alkyl is optionally substituted with aryl;
wherein said aryl is optionally substituted with $C_{1-6}$alkyl, $C_{2-6}$alkenyl, $C_{2-6}$alkynyl, halo, nitro, hydroxyl, ethynyl, —CN, aryl, —$SO_3H$, —C(O)OH, —C(O)O—$C_{1-4}$alkyl, —C(O)NR'R", —SR', —OR', —C(O)R', —N(R')(R"), —S(O)$_2$—R', and —S(O)$_2$—N(R')(R"), wherein R' and R" are independently selected from H, $C_{1-6}$-alkyl, and aryl;
$R_2$ is 0-3 members independently selected from halo, —$OR_4$, —$SR_4$, —S(O)$_2$—$R_4$, carboxy, nitro, hydroxyl, amido, $C_{1-6}$alkyl, $C_{2-6}$alkenyl, $C_{2-6}$alkynyl, and amino $C_{1-6}$alkyl, or aryl, wherein $R_4$ is selected from H, $C_{1-6}$alkyl, and aryl; and
wherein the $C_{1-6}$alkyl is optionally substituted with aryl;
wherein the $C_{2-6}$alkenyl is optionally substituted with one to three groups selected from amino, alkoxy, carboxy, nitro, hydroxyl, and halo;
wherein the amino is optionally substituted with $C_{1-6}$alkyl, and aryl;
wherein said $C_{1-6}$alkyl is optionally substituted with aryl;
wherein said aryl is optionally substituted with $C_{1-6}$alkyl, $C_{2-6}$alkenyl, $C_{2-6}$alkynyl, halo, nitro, hydroxyl, ethynyl, —CN, aryl, —$SO_3H$, —C(O)OH, —C(O)O—$C_{1-4}$alkyl, —C(O)NR'R", —SR', —OR', —C(O)R', —N(R')(R"), —S(O)$_2$—R', and —S(O)$_2$ —N(R')(R"), wherein R' and R" are independently selected from H, $C_{1-6}$-alkyl, and aryl;

A is pyridine, said pyridine being connected to N(1) through a ring carbon atom adjacent to a ring nitrogen, and said pyridine being further optionally substituted with 1 or 2 members selected from $C_{1-4}$alkyl, $C_{2-4}$alkenyl, halo, —CN, aryl, —SO$_3$H, —C(O)OH, —C(O)O—$C_{1-4}$alkyl, —OR$_4$, —SR$_4$, —C(O)R$_4$, —N(R$_4$)(R$_5$), —C(O)—N(R$_4$)(R$_5$), —S(O)$_2$—R$_4$, and —S(O)$_2$—N(R$_4$)(R$_5$), wherein R$_4$ and R$_5$ are independently selected from H, $C_{1-6}$-alkyl, and aryl;

wherein the $C_{1-4}$alkyl is optionally substituted with aryl;

wherein the $C_{2-4}$alkenyl is optionally substituted with one to three groups selected from amino, alkoxy, carboxy, nitro, hydroxyl, and halo;

or an optical isomer, enantiomer, diastereomer, racemate or pharmaceutically acceptable salt thereof.

2. The compound of claim 1 wherein

R$_1$ is $C_{1-6}$alkyl, wherein the $C_{1-6}$alkyl is optionally substituted with $C_6$- or $C_{10}$-aryl;

wherein said $C_6$- or $C_{10}$-aryl is optionally substituted with $C_{1-6}$alkyl, $C_{2-6}$alkenyl, $C_{2-6}$alkynyl, halo, nitro, hydroxyl, ethynyl, —CN, aryl, —SO$_3$H, —C(O)OH, —C(O)O—$C_{1-4}$-alkyl, —C(O)NR'R"—, —SR', —OR', —C(O)R', —N(R')(R"), —S(O)$_2$—R', and —S(O)$_2$—N(R')(R"), wherein R' and R" are independently selected from H, $C_{1-6}$-alkyl, and aryl;

A is pyridine, said pyridine being connected to N(1) through a ring carbon atom adjacent to a ring nitrogen, and said pyridine being further optionally substituted with 1 or 2 members selected from $C_{1-4}$-alkyl, $C_{2-4}$alkenyl, halo, —CN, $C_{6-10}$aryl, —C(O)OH, —C(O)O—$C_{1-4}$alkyl, —OR$_4$, —C(O)R$_4$, —SR$_4$, —C(O)—N(R$_4$)(R$_5$), —S(O)$_2$—R$_4$, and —S(O)$_2$—N(R$_4$)(R$_5$), wherein R$_4$ and R$_5$ are independently selected from H, $C_{1-6}$alkyl, and aryl;

wherein said $C_{1-4}$alkyl is optionally substituted with one to three groups selected from oxo, amino, alkoxy, carboxy, nitro, hydroxyl, and halo, wherein said $C_{2-4}$alkenyl is optionally substituted with one to three groups selected from alkoxy, carboxy, nitro, hydroxyl, and halo;

wherein said $C_{6-10}$aryl is optionally substituted with $C_{1-6}$alkyl, $C_{2-6}$alkenyl, $C_{2-6}$alkynyl, halo, nitro, hydroxyl, ethynyl, —CN, aryl, —SO$_3$H, —C(O)OH, —C(O)O—$C_{1-4}$-alkyl, —C(O)NR'R"—, —SR', —OR', —C(O)R', —N(R')(R"), —S(O)$_2$—R', and —S(O)$_2$—N(R')(R"), wherein R' and R" are independently selected from H, $C_{1-6}$-alkyl, and aryl;

X is $C_{1-2}$ alkylene; and

Y is S;

or an optical isomer, enantiomer, diastereomer, racemate or pharmaceutically acceptable salt thereof.

3. The compound of claim 1 or 2 wherein R$_1$ is methyl substituted with phenyl, said phenyl optionally substituted with OH, $C_{1-3}$alkyl, —N(R$_4$)(R$_5$), halo, alkoxy, —C(O)O—$C_{1-4}$alkyl, or —NO$_2$.

4. The compound of claim 1 wherein A is

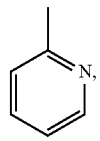

wherein said

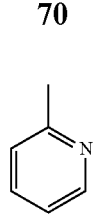

is optionally substituted with $C_{1-6}$alkyl, $C_{2-6}$alkenyl, $C_{2-6}$alkynyl, halo, nitro, hydroxyl, ethynyl, —CN, aryl, —SO$_3$H, —C(O)OH, —C(O)O—$C_{1-4}$-alkyl, —C(O)NR'R"—OR', —SR'—C(O)R', —N(R')(R"), —S(O)$_2$—R', and —S(O)$_2$—N(R')(R"), wherein R' and R" are independently selected from H, $C_{1-6}$-alkyl, and aryl.

5. The compound of claim 4 wherein A is substituted with 0-2 members selected from halo, $C_{1-4}$-alkyl, —CN, aryl, —C(O)OH, —C(O)R$_4$, —C(O)O—$C_{1-4}$alkyl, —C(O)—N(R$_4$)(R$_5$), and —S(O)$_2$—N(R$_4$)(R$_5$), wherein said $C_{1-a}$alkyl is optionally substituted with one to three groups selected from oxo, amino, alkoxy, carboxy, nitro, hydroxyl, and halo, wherein said aryl is optionally substituted with $C_{1-6}$alkyl, $C_{2-6}$alkenyl, $C_{2-6}$alkynyl, halo, nitro, hydroxyl, ethynyl, —CN, aryl, —SO$_3$H, —C(O)OH, —C(O)O—$C_{1-4}$alkyl, —C(O)NR'R"—OR', —SR'—C(O)R', —N(R')(R"), —S(O)$_2$—R', and —S(O)$_2$—N(R')(R"), wherein R' and R" are independently selected from H, $C_{1-6}$-alkyl, and aryl.

6. The compound of claim 5 wherein A is substituted with 0-2 members selected from F, Cl, Br, —CH$_3$, —CH$_2$—CH$_3$, —CF$_3$, —CH$_2$—C(O)OH, —CN, —C(O)—CH$_3$, —CH$_2$—O—CH$_2$—O—CH$_3$, unsubstituted phenyl, halo substituted aryl, —C(O)OH, —C(O)O—CH$_3$, —CH$_2$—C(O)O—CH$_2$—CH$_3$, —C(O)O—CH$_2$—CH$_3$, —C(O)—NH$_2$, and —S(O)$_2$—NH$_2$.

7. The compound of claim 1 wherein X is $C_{1-2}$ alkylene, wherein said $C_{1-2}$ alkylene is optionally substituted with one to three groups selected from alkoxy, carboxy, nitro, hydroxyl, and halo.

8. The compound of claim 7 wherein X is —C(H)(CH$_3$)— or —CH$_2$—.

9. The compound of claim 1 wherein Y is S.

10. The compound of claim 1 selected from

6-{2-[1-(4-Methoxy-benzyl)-3,4-dimethyl-5-oxo-2,5-dihydro-1H-pyrrol-2-ylsulfanyl]-acetylamino}-nicotinic acid methyl ester;

6-{2-[1-(4-Methoxy-benzyl)-3,4-dimethyl-5-oxo-2,5-dihydro-1H-pyrrol-2-ylsulfanyl]-acetylamino}-nicotinic acid;

6-{2-[1-(4-Fluoro-benzyl)-3,4-dimethyl-5-oxo-2,5-dihydro-1H-pyrrol-2-ylsulfanyl]-acetylamino}-nicotinic acid methyl ester; and 6-{2-[1-(2,3-Dihydro-benzofuran-5-ylmethyl)-3,4-dimethyl-5-oxo-2,5-dihydro-1H-pyrrol-2-ylsulfanyl]-acetylamino}-nicotinic acid methyl ester 11. The compound of claim 1, wherein R$_1$ is —CH$_2$—OR—CH(CH$_3$)— substituted with

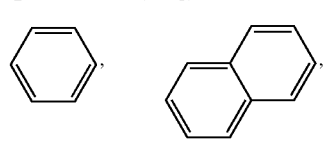

said

, or

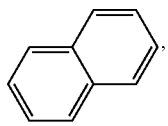, being optionally substituted with F, OH, —CH$_3$, —O—CH$_3$, —NO$_2$, —O—CH(CH$_3$)$_2$, and —C(O)—NH$_2$;

A is

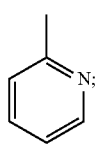

and

X is methylene.

12. The compound of claim 11 wherein A is substituted with 0-2 members selected from halo, C$_{1-4}$alkyl, aryl, —C(O)OH, —C(O)R$_4$, —C(O)—N(R$_4$)(R$_5$), —C(O)O—C$_{1-4}$alkyl, and —S(O)$_2$—N(R$_4$)(R$_5$)

wherein said C$_{1-4}$alkyl is optionally substituted with one to three groups selected from oxo, amino, alkoxy, carboxy, nitro, hydroxyl, and halo, wherein said aryl is optionally substituted with C$_{1-6}$alkyl, C$_{2-6}$alkenyl, C$_{2-6}$alkynyl, halo, nitro, hydroxyl, ethynyl, —CN, aryl, —SO$_3$H, —C(O)OH, —C(O)O—C$_{1-4}$alkyl, —C(O)NR'R"—OR', —SR'—C(O)R', —N(R')(R"), —S(O)$_2$—R', and —S(O)$_2$—N(R')(R"), wherein R' and R" are independently selected from H, C$_{1-6}$-alkyl, and aryl, wherein said C$_{1-6}$alkyl is optionally substituted with one to three groups selected from oxo, amino, alkoxy, carboxy, nitro, hydroxyl, and halo.

13. The compound of claim 12 wherein A is substituted with 0-2 members selected from —CH$_3$, —C(O)OH, —C(O)O—CH$_3$, and —C(O)—NH$_2$.

14. A pharmaceutical composition comprising one or more compounds of claim 1 and at least one pharmaceutically acceptable carrier.

* * * * *